United States Patent
Fan et al.

(10) Patent No.: US 11,154,512 B2
(45) Date of Patent: Oct. 26, 2021

(54) HEMOSTATIC COMPOUND AND PREPARATION METHOD THEREOF

(71) Applicant: Zhejiang University, Hangzhou (CN)

(72) Inventors: Jie Fan, Hangzhou (CN); Lisha Yu, Hangzhou (CN); Liping Xiao, Hangzhou (CN); Hao Chen, Hangzhou (CN); Xiaoqiang Shang, Hangzhou (CN)

(73) Assignee: Hangzhou Zeo-Innov Life Technology Co., Ltd, Hangzhou (CN)

( * ) Notice: Subject to any disclaimer, the term of this patent is extended or adjusted under 35 U.S.C. 154(b) by 0 days.

(21) Appl. No.: 16/842,753

(22) Filed: Apr. 7, 2020

(65) Prior Publication Data
US 2020/0237681 A1    Jul. 30, 2020

Related U.S. Application Data

(63) Continuation of application No. PCT/CN2019/082931, filed on Apr. 16, 2019.

(51) Int. Cl.
  *A61K 9/70* (2006.01)
  *A61P 7/04* (2006.01)
  *A61K 45/06* (2006.01)

(52) U.S. Cl.
  CPC ............ *A61K 9/7007* (2013.01); *A61K 45/06* (2013.01); *A61P 7/04* (2018.01)

(58) Field of Classification Search
  None
  See application file for complete search history.

(56) References Cited

U.S. PATENT DOCUMENTS

| | | | |
|---|---|---|---|
| 7,390,452 B2 | 6/2008 | Balkus, Jr. et al. | |
| 2007/0104768 A1* | 5/2007 | Huey | A61L 15/18 424/443 |

(Continued)

FOREIGN PATENT DOCUMENTS

| | | |
|---|---|---|
| CN | 1779004 A | 5/2006 |
| CN | 101036591 A | 9/2007 |

(Continued)

OTHER PUBLICATIONS

The effects of zeolite molecular sieve based surface treatments on the properties of wool fabrics, Richard S. Carran, et al. Applied Surface Science 287(2013) 467-472.

(Continued)

*Primary Examiner* — Kyung S Chang
(74) *Attorney, Agent, or Firm* — Wen IP LLC; Zhihua Han

(57) ABSTRACT

A hemostatic compound is provided. The hemostatic compound comprises molecular sieves and a fiber. The molecular sieves are independently dispersed on a fiber surface of the fiber without agglomeration and directly contact the fiber surface. A first surface of the molecular sieve contacted with the fiber is defined as an inner surface, and a second surface of the molecular sieve uncontacted with the fiber is defined as an outer surface. The molecular sieve forms a growth-matched coupling with the fiber on the inner surface, and the growth-matched coupling refers to that a plurality of molecular sieve microparticles grow to match the fiber surface to form a tightly-coupled coupling interface that matches the fiber surface.

18 Claims, 12 Drawing Sheets

(56) References Cited

U.S. PATENT DOCUMENTS

| | | | | |
|---|---|---|---|---|
| 2007/0154510 A1* | 7/2007 | Wilcher | ............... | A61L 15/18 |
| | | | | 424/422 |
| 2008/0199539 A1* | 8/2008 | Baker | ............... | A61L 15/44 |
| | | | | 424/684 |
| 2009/0186071 A1* | 7/2009 | Huey | ............... | A61P 29/00 |
| | | | | 424/446 |

FOREIGN PATENT DOCUMENTS

| | | |
|---|---|---|
| CN | 103449473 A | 12/2013 |
| CN | 104846371 A | 8/2015 |
| CN | 104888267 A | 9/2015 |
| WO | WO2007033135 A2 | 3/2007 |

OTHER PUBLICATIONS

Antimicrobial Activity of Silver Ions Released from Zeolites Immobilized on Cellulose Nanofiber Mats, Katrina A. et al. Applied Materials & Interfaces, 2016, 8, 3032-3040.
Preparation of Flexible Zeolite-Tethering Vegetable Fibers, Goo Soo Lee, et al. Advanced Materials, 2001. 13. No. 19, Oct. 2, 1491-1495.
Ceramic papers containing Y zeolite for toluene removal, Juan Pablo Cecchini, et al. Microporous and MesoporousMaterials 145(2011) 51-58.
ISR of PCT/CN2019/082931.

* cited by examiner

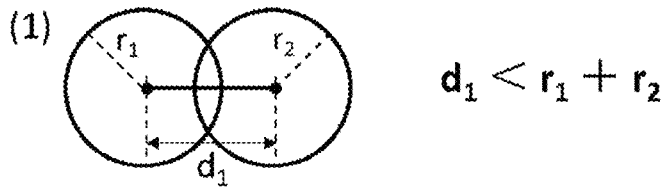

○ Molecular sieve microparticle model $r_1$, $r_2$ represent one half of the particle size of the molecular sieve microparticles ; $d_1$, $d_2$, $d_3$ represent the minimum distance between the molecular sieve microparticles and the nearest molecular sieve microparticles.

Figure 20A

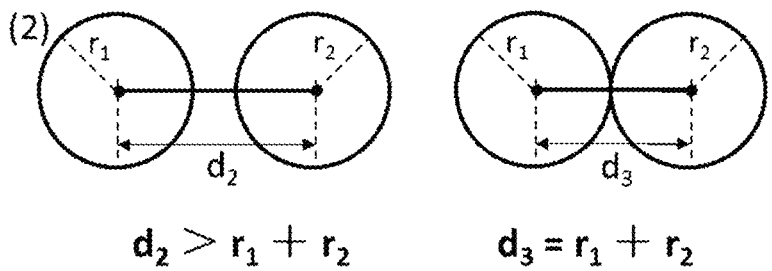

○ Molecular sieve microparticle model $r_1$, $r_2$ represent one half of the particle size of the molecular sieve microparticles ; $d_1$, $d_2$, $d_3$ represent the minimum distance between the molecular sieve microparticles and the nearest molecular sieve microparticles.

Figure 20B

HEMOSTATIC COMPOUND AND PREPARATION METHOD THEREOF

CROSS REFERENCE OF RELATED APPLICATIONS

This application is a continuation of PCT Patent Application No. PCT/CN2019/082931, filed on Apr. 16, 2019, entitled "HEMOSTATIC COMPOUND AND PREPARATION METHOD THEREOF," which claims foreign priority of China Patent Application No. 201810625854.7, filed Jun. 18, 2018 in the China National Intellectual Property Administration, the entire contents of which are hereby incorporated by reference in their entireties.

TECHNICAL FIELD

The disclosure relates to the technical field of biomedical materials, and particularly relates to a hemostatic compound and a preparation method thereof.

BACKGROUND

Humans (including animals) can be injured in a variety of situations. In some cases, the trauma and bleeding are minor, and in addition to the application of simple first aid, only regular coagulation is required to stop bleeding normally. Unfortunately, however, massive bleeding can occur in other settings. These situations often require specialized equipment and materials, and professionally trained personnel to implement appropriate assistance. If such assistance is not readily available, excessive blood loss may result in death. Bleeding is a very serious global problem. It is estimated that 1.9 million people worldwide die from bleeding every year, of which 1.5 million die from physical trauma. Among them, the deaths of these 1.5 million people have caused nearly 75 million years of lost life worldwide, which is about half of the life loss caused by cancer (170 million years). Therefore, in the emergency treatment of sudden accidents in daily life, the hemostasis during the operation of the hospital to the patient, especially the rescue of the wounded soldiers during the war, the effective rapid hemostasis for the patient is very important.

Molecular sieves have good hemostatic effects, are suitable for emergency hemostasis, especially aortic bleeding, and are cheap, stable, and easy to carry. A substance with a regular microporous channel structure and a function of screening molecules is called molecular sieve. $TO_4$ tetrahedron (T is selected from Si, Al, P, B, Ga, Ge, etc.) is the most basic structural unit ($SiO_4$, $AlO_4$, $PO_4$, $BO_4$, $GaO_4$, $GeO_4$, etc.) constituting the molecular sieve skeleton, which is bound by a common oxygen atom to form a three-dimensional network structure. This combination forms holes and pores with a molecular level and a uniform pore size. Skeleton T atoms usually refer to Si, Al or P atoms, and in a few cases to other atoms, such as B, Ga, Ge, etc. For example, a zeolite is an aluminosilicate molecular sieve, which is an aluminosilicate with the ability of sieving molecules, adsorption, ion exchange, and catalysis. The general chemical composition of zeolite is: $(M)_{2/n}O \cdot xAl_2O_3 \cdot ySiO_2 \cdot pH_2O$, M stands for metal ion (such as $K^+$, $Na^+$, $Ca^{2+}$, $Ba^{2+}$, etc.), n stands for valence of metal ion, and x stands for mole of $Al_2O_3$, Y represents the mole number of $SiO_2$, and p represents the mole number of $H_2O$. The molecular sieve may be X-type molecular sieve, Y-type molecular sieve, A-type molecular sieve, ZSM-5 molecular sieve, chabazite, beta molecular sieve, mordenite, L-type molecular sieve, P-type molecular sieve, merlinoite, AlPO4-5 molecular sieve, AlPO4-11 molecular sieve, SAPO-31 molecular sieve, SAPO-34 molecular sieve, SAPO-11 molecular sieve, BAC-1 molecular sieve, BAC-3 molecular sieve, or BAC-10 molecular sieve.

Molecular sieves rely on van der Waals forces during the adsorption process. The distance between molecules during the mutual attraction process is reduced, and the potential energy of the molecules is converted to internal energy to release energy. Therefore, the molecular sieve absorbs water and releases heat. In the prior art, molecular sieves mainly cover wounds in the form of granules or powder to stop bleeding, and the wounded may feel uncomfortable. Because the hemostatic material needs to completely cover the wound, powder and granular molecular sieves are used as hemostatic materials in very large amounts, which causes the molecular sieve to absorb a large amount of water and exotherm on the wound and easily burn the wound. During use, the molecular sieve will stick to the wound, which is very difficult to clean. It needs multiple flushes to remove it, which easily leads to secondary bleeding. The granular molecular sieve needs to be adhered by an adhesive so that the molecular sieve cannot contact the blood of the wound sufficiently, which affects the hemostatic effect of molecular sieve. At the same time, during the use of powder and granular molecular sieve, due to direct contact with the wound, the molecular sieve adhered on the wound has the risk of entering blood vessels or other tissues, and it is easy to remain in the lumen of the blood vessel to form a thrombus to block peripheral artery flow.

In order to facilitate the use of molecular sieves in hemostasis, the molecular sieves need to be supported on a suitable support. Fiber has good physical properties such as flexibility, elasticity, strength, and weavability. It is one of the ideal choices for molecular sieve carriers. Inorganic fibers are mainly glass fibers, quartz glass fibers, carbon fibers, boron fibers, ceramic fibers, metal fibers, silicon carbide fibers, and the like. The surface compounds of some inorganic fibers (such as silica fibers) can chemically react with molecular sieves, which can cause molecular sieves to bind to the surface of inorganic fibers. However, inorganic fibers are brittle, easy to break, and easy to wear, which makes them unsuitable as a flexible carrier for molecular sieves. Therefore, inorganic fibers are not within the scope of the fibers described in the present disclosure. The fibers in the present disclosure refer to organic fibers. The organic fibers can be divided into two categories: one is natural fiber, such as cotton, wool, silk, and hemp; the other is chemical fiber, which is made by chemical processing of natural or synthetic polymer compounds. According to the source and chemical structure of the polymer, chemical fiber can be divided into artificial fiber and synthetic fiber. Artificial fibers are divided into regenerated protein fibers, regenerated cellulose fibers, and cellulosic fibers. Synthetic fibers are divided into carbon chain fibers (the macromolecule main chain is composed of C—C) and heterochain fibers (the macromolecule main chain contains other elements, such as N, O, etc.). Carbon chain fibers include polyacrylonitrile fibers, polyvinyl acetal fibers, polyvinyl chloride fibers, fluorine-containing fibers and so on. Heterochain fibers include polyamide fibers, polyester fibers, polyurethane elastic fibers, polyurea fibers, polytoluene fibers, polyimide fibers, polyamide-polyhydrazine fibers, polybenzimidazole fibers, and so on. For organic fibers, because the polar groups (such as hydroxyl group) on the fiber surface are inert and inactive, the interaction between the molecular sieve and the fiber is very weak. At present, most molecular sieves are sprayed or impregnated on the fibers. The molecular sieves and fibers are simply physically mixed, and the binding force is weak. As a result, the molecular sieve on the fiber has less adsorption and is easy to fall off. In the prior art, in order to better combine molecular sieves on the fiber surface, pretreatment of the fibers (destruction of fiber structure), adhesive bonding, and blend spinning of molecular sieve and fiber are used:

(1) Pretreatment of the fibers. The pretreatment refers to a treatment method that destroys the fiber structure. In the prior art, in order to enable the molecular sieve to be directly bonded to the fiber, the fiber must be pretreated first. Pretreatment methods mainly include chemical treatment, mechanical treatment, ultrasonic treatment, microwave treatment, and so on. The method of chemical treatment is divided into treatment with a base compound, an acid compound, an organic solvent, etc. The base compound may be selected from any one or more of NaOH, KOH, $Na_2SiO_3$, etc. The acid compound may be selected from any one or more of hydrochloric acid, sulfuric acid, nitric acid, etc. The organic solvent may be selected from any one or more of ether, acetone, ethanol etc. Mechanical treatment can be by crushing or grinding fibers. The above-mentioned fiber treatment methods, although the pretreatment to a certain extent activates the polar groups (such as hydroxyl group) on the fiber surface, but seriously damages the structure of the fiber (FIG. 1), destroying the fiber flexibility, elasticity and other characteristics. The fiber becomes brittle, hard and other bad phenomena, and can not give full play to the advantages of fiber as a carrier. In addition, pretreatment of the fibers will cause molecular sieves to aggregate on the fiber surface. For example, molecular sieves are wrapped on the fiber surface with agglomerates or massive structures (FIGS. 2 and 3), resulting in poor fiber flexibility of fiber; or molecular sieves are partially agglomerated and unevenly distributed on the fiber surface (FIG. 4); or there is a gap between the fiber and the molecular sieve (FIG. 5), and the force between the molecular sieve and the fiber is weak. The aggregation of molecular sieves on the fiber surface will lead to uneven distribution of molecular sieves on the fiber surface, and cause differences in the properties of hemostatic complexes, reducing the original specific surface area of the molecular sieve, leading to blockage of the molecular sieve channels and lowering the ability of ion exchange and pore material exchange. The pretreatment of the fiber surface is at the cost of destroying the fiber structure. Although the interaction force between the part of fiber and the molecular sieve is enhanced to form a molecular sieve/fiber composite to a certain extent, the interaction force is still not strong enough. Under external conditions, for example, a simple washing method will also cause a large number (50-60%) of molecular sieves to fall off the fiber surface (Microporous & Mesoporous Materials, 2002, 55 (1): 93-101 and US20040028900A1).

(2) Adhesive bonding. In order to increase the bonding strength between the molecular sieve and the fiber, the prior art mainly uses the adhesive to interact with the molecular sieve and the fiber to form a sandwich-like structure, and the middle layer is the adhesive, so that the molecular sieve can be indirectly bonded through the adhesive on the fiber (FIG. 16). Adhesive is a substance with a stickiness that relies on a chemical reaction or physical action as a medium to connect the separated molecular sieve and the fiber material together through a binder. For adhesives, the main disadvantages include: (1) the quality of the joint cannot be inspected with the naked eye; (2) careful surface treatment of the adherend is required, such as chemical corrosion methods; (3) long curing time is needed; (4) the temperature used is too low, and the upper temperature limit for general adhesives is about 177° C., and the upper temperature limit for special adhesives is about 371° C.; (5) most adhesives require strict process control, and especially the cleanliness of the bonding surface is higher; (6) the service life of the bonding joint depends on the environment, such as humidity, temperature, ventilation and so on. In order to ensure that the performance of the adhesive is basically unchanged within the specified period, strict attention must be paid to the method of storing the adhesive. For molecular sieves, the main disadvantages of using adhesive include: (i) uneven distribution of molecular sieves on the fiber surface; (ii) easy agglomeration of molecular sieves, reducing the effective surface area of molecular sieves, and possibly causing blockage of molecular sieve channels, and reducing ion exchange of molecular sieves, and leading to poor transfer of materials and high cost of synthetic molecular sieves. In addition, the addition of the adhesive does not significantly increase the load of the molecular sieve on the fiber; does not greatly enhance the binding of the molecular sieve to the fiber. And the molecular sieves still easily fall off the fiber surface.

Adhesives are divided according to material source: (i) natural adhesives, including starch, protein, dextrin, animal gum, shellac, skin rubber, bone glue, natural rubber, rosin and other biological adhesives, and also include asphalt and other mineral adhesives; (ii) synthetic adhesives, mainly refers to synthetic substances, including inorganic binders such as silicate, phosphate; and epoxy resin, phenolic resin, urea resin, polyvinyl alcohol, polyurethane, polyetherimide, polyvinyl acetal, perchloroethylene resin and other resins; neoprene, nitrile rubber and other synthetic polymer compounds. According to the use characteristics: (1) water-soluble adhesives, such as starch, dextrin, polyvinyl alcohol, carboxymethyl cellulose, etc.; (2) hot-melt adhesives, such as polyurethane, polystyrene, polyacrylate, ethylene-vinyl acetate copolymer, etc.; (3) solvent-based adhesives, such as shellac, butyl rubber, etc.; (4) emulsion adhesive, mostly suspended in water, such as vinyl acetate resin, acrylic resin, chlorinated rubber, etc.; (5) solvent-free liquid adhesive, which is a viscous liquid at normal temperature, such as epoxy resin, etc. According to raw materials: (i) MS modified silane, the end of the modified silane polymer is methoxysilane; (ii) polyurethane, the full name of polyurethane is a collective name for macromolecular compounds containing repeating urethane groups on the main chain; (iii) silicones are commonly referred to as silicone oil or dimethyl silicone oil. The molecular formula is $(CH_3)_3SiO(CH_3)_2SiO_nSi(CH_3)_3$. It is a polymer of organic silicon oxide and a series of polydimethylsiloxanes with different molecular weight, of which viscosity increases with molecular weight.

The paper discloses an adhesive-bonded A-type molecular sieve/wool fiber composite (Applied Surface Science, 2013, 287 (18): 467-472). In this composite, 3-mercaptopropyltrimethoxysilane is used as a binder, and the A-type molecular sieve is bonded to the surface of the wool fiber, and the content of the A-type molecular sieve on the fiber is 2.5% or less. After the silane binder was added, agglomerated molecular sieves appeared on the surface of wool fibers, which was observed through scanning electron microscopy. The active silane binder caused agglomeration of molecular sieve particles. The agglomeration of molecular sieve particles will reduce the effective surface area of the molecular sieve and the ability of material exchange.

The paper discloses an adhesive-bonded Na-LTA molecular sieve/nanocellulose fiber composite (ACS Appl. Mater. Interfaces 2016, 8, 3032-3040). In this composite, nanocellulose fibers were immersed in a polydiallyl dimethyl ammonium chloride (polyDADMAC) aqueous solution at 60° C. for 30 minutes to achieve adsorption of LTA molecular sieves (polyDADMAC is an adhesvie). Although molecular sieves can be attached to the fiber surface by polycation adsorption of polyDADMAC, for nano Na-LTA at 150 nm, mesoporous Na-LTA and micron-sized Na-LTA on the fiber, the content is only 2.6±0.6 wt % (coefficient of variation is 23.1%, calculation method is 0.6×100%/2.6=23.1%), 2.9±0.9 wt % (coefficient of variation is 31.0%), and 12.5±3.5 wt % (coefficient of variation is 28%), respectively. The molecular sieve is unevenly distributed on the fiber surface, which is difficult to achieve equal content of molecular sieve on fiber surface. Coefficient of variance is also called the "standard deviation rate", which is the ratio of the standard deviation to the mean multiplied by 100%. Coefficient of variation is an absolute value that reflects the degree of dispersion of the data. The higher the coefficient of variation, the greater the degree of dispersion of the data, indicating that the content of molecular sieves varies widely across the fiber surface. From the scanning electron microscope, it can be observed that the Na-LTA molecular sieve does not form a binding interface with the fiber (FIG. 6), indicating that the bonding between the fiber and the molecular sieve is not strong, and the molecular sieve is easy to fall off the fiber surface.

The paper discloses a Y-type molecular sieve/fiber composite bonded by an adhesive (Advanced Materials, 2010, 13 (19): 1491-1495). Although molecular sieves can be attached to the surface of plant fibers by covalent bonds of the binder, the amount of adhesion is limited (all below 5 wt %). In this composite, 3-chloropropyltrimethoxysilane was used as a binder to modify the surface of the molecular sieve to make it adhere to cotton fibers. And it fell off by 39.8% under ultrasonic conditions for 10 minutes (the retention rate of the molecular sieve on the fibers was 60.2%); it fell off by 95% under ultrasonic conditions for 60 minutes (the retention rate of the molecular sieve on the fibers was 5%), which indicates that the chemical bonding between the molecular sieve and the fiber is not strong in this technology. In order to increase the bonding strength between molecular sieve and fiber, this technology modifies polyetherimide as a binder to the fiber surface, and then attaches 3-chloropropyltrimethoxysilane-modified molecular sieve to the binder-modified fiber. Although the adhesive strength of the fiber and molecular sieve is increased to some extent under this condition, it still falls off under ultrasonic conditions. For this composite material, both the surface of the molecular sieve and the fiber interact with the binder, and the sandwich-like material is formed by the adhesive of the intermediate layer, which increases the cost of the synthesis process and reduces the effective surface area of the molecular sieve.

The paper discloses a NaY-type molecular sieve/fiber composite bonded by a cationic and anionic polymer binder (Microporous & Mesoporous Materials, 2011, 145 (1-3): 51-58). NaY molecular sieves are added to cellulose and polyvinyl alcohol amine solution, and then polyacrylamide polymer solution is added to form corresponding composite materials. Scanning electron microscopy can observe that there is no bond between NaY molecular sieve and fiber, and there is no force between them. It is just a simple physical combination of the two materials so that the molecular sieve can easily fall off the fiber (FIG. 7).

(3) Blend spinning of molecular sieve and fiber. The solution of molecular sieve and the solution of synthetic fiber are mixed uniformly for spinning, and the molecular sieve and fiber are simply physically combined. Molecular sieves are mostly present in the fibers and are not bound to the fiber surface (FIG. 8).

U.S. Pat. No. 7,390,452B2 discloses an electrospun mesoporous molecular sieve/fiber composite. Polyetherimide (PEI) methanol solution and mesoporous molecular sieve solution were electrospun to form a composite. No molecular sieve was apparently observed on the fiber surface from the scanning electron microscope (FIG. 9), which suggests most of the molecular sieve was present inside the fiber, and the internal molecular sieve was unable to exert its performance.

Chinese patent CN1779004A discloses an antibacterial viscose fiber and its preparation method. The disclosure is prepared by blending and spinning a silver molecular sieve antibacterial agent and a cellulose sulfonate solution, and the silver molecular sieve antibacterial agent accounts for 0.5 to 5% of cellulose. The silver molecular sieve is dispersed in a cellulose sulfonate solution through a 0.01% MET dispersant, and spin-molded at a bath temperature of 49° C. Most of the molecular sieve exists in the fiber, which easily blocks the molecular sieve channels, resulting in a small effective surface area.

Chinese patent CN104888267A discloses a medical hemostatic spandex fiber and a preparation method thereof. The method for preparing medical hemostatic spandex fiber includes the following steps: (i) preparing a polyurethane urea stock solution; (ii) grinding the inorganic hemostatic powder and dispersant in a dimethylacetamide solvent to obtain a hemostatic solution; (iii) placing the polyurethane urea stock solution and hemostatic solution in a reaction container, and weaving them into a spandex fiber through a dry spinning process. The inorganic hemostatic powder is one or more of diatomite, montmorillonite, zeolite, bioglass and halloysite nanotubes. A large part of the inorganic hemostatic powder in the hemostatic spandex fiber is inside the fiber, which cannot fully contact with the blood and cannot exert its hemostatic effect. Although the amount of inorganic hemostatic powder is increased, the hemostatic effect is not good.

In addition, Z-Medica Co., Ltd. developed Combat Gauze, a hemostatic product known as a "life-saving artifact". This product is an emergency hemostatic product recommended by Committee on Tactical Combat Casualty Care (Co-TCCC) for the US military. At present, it is used as an important first-aid device for military equipment and ambulances. U.S. Pat. No. 8,114,433B2, Chinese patent CN101541274B, and CN101687056B disclose that the technology of this type of hemostatic product is a device capable of providing hemostatic effect on bleeding wounds, using an adhesive to attach a clay material to the surface of gauze. However, the adhesive not only reduces the contact area of the clay material with the blood, but also has a weak binding strength between the clay material and the gauze fibers. After the hemostatic material (clay/fiber composite) product encounters water, the clay material on the gauze surface is still very easy to fall off the gauze fiber (FIG. 18). Clay retention rate on the gauze fiber is 10% or less under ultrasonic condition for 1 minute; clay retention rate on the gauze fiber is 5% or less under ultrasonic condition for 5 minutes (FIG. 19); clay retention rate on the gauze fiber is 5% or less under ultrasonic condition for 20 minutes. This defective structural form limits the hemostatic properties of the hemostatic product and risks causing sequelae or other side effects (such as thrombus).

Dispersing molecular sieves (or inorganic hemostatic materials) on the fibers in a small size can solve the problem of molecular sieve materials sticking to the wound and the difficulty of cleaning up the wound to a certain extent, reduce the amount of molecular sieves, and dilute the exothermic effect caused by water absorption. However, the existing molecular sieves and fiber composites are used as hemostatic fabric materials, and the hemostatic composites prepared in the prior art have four structural forms: (1) physical mixing of molecular sieves and fibers; (2) aggregation of molecular sieves formed on the fiber surface; (3) molecular sieve and the fiber form a sandwich-like structure through an adhesive; (4) most of the molecular sieve is present inside the fiber and is not bound to the fiber surface. The composite materials of these four structural forms have poor dispersibility of the molecular sieve, small effective specific surface area, insufficient contact with blood during use, and poor hemostatic effect. The effective specific surface area of the molecular sieve in the molecular sieve and fiber hemostatic composite is smaller than the original effective specific surface area of the molecular sieve. Among the first three types of composite materials, molecular sieves easily fall off the fiber surface, and the retention rate of molecular sieves is low, and the hemostatic material easily loses the hemostatic effect. Some detached molecular sieves will stick to the wound and some will enter the blood circulation. Molecular sieves tend to remain in blood vessels, inducing the risk of thrombosis. On the other hand, the properties of silicate inorganic hemostatic materials (e.g. clay) are similar to molecular sieves. The composite materials formed by inorganic hemostatic materials and fibers also have the above-mentioned four defective structural forms, which seriously affects the performance and safety of hemostatic materials. Without the addition of an adhesive, the prior art cannot achieve a strong binding between the molecular sieve (or inorganic hemostatic material) and the fiber, cannot prevent molecular sieve fall off, cannot achieve good dispersibility of molecular sieve on the fiber surface, and cannot remain effective specific surface area of molecular sieve and cannot possess excellent hemostatic function of molecular sieve and fiber composite.

SUMMARY

In view of the shortcomings of the prior art, the first technical problem to be solved by the present disclosure is to provide a hemostatic compound with strong binding between molecular sieve and fiber, high hemostatic performance and high safety during the hemostatic process without adding an adhesive, and the molecular sieve in the hemostatic compound maintains the original large effective specific surface area and strong substance exchange capacity of pore.

The present disclosure adopts the following technical solutions:

The present disclosure provides a novel hemostatic material by a simple method. The hemostatic material is a hemostatic compound, which comprises a molecular sieve and a fiber, and the molecular sieve is distributed on the fiber surface and directly contacts the fiber surface. The particle diameter D90 of the molecular sieve is 0.01 to 50 μm, the particle diameter D50 of the molecular sieve is 0.005 to 30 μm. The adhesive content of the contact surface between the molecular sieve and the fiber is zero. The surface of molecular sieve contacted with the fiber is inner surface, and the inner surface is a rough planar surface matched with the fiber surface, and growth-matched coupling is formed between the molecular sieve and the fiber on the inner surface of the molecular sieve. The surface of molecular sieve uncontacted with the fiber is outer surface, and the outer surface is non-planar surface. Both the inner surface and outer surface are composed of molecular sieve nanoparticles.

D50 refers to the particle size corresponding to the cumulative particle size distribution percentage of the molecular sieve microparticles on the surface of the hemostatic compound reaching 50%. Its physical meaning is that molecular sieve microparticles with a particle size larger than it account for 50%, and molecular sieve microparticles with a particle size smaller than it also account for 50%. D50 is also called median particle size, which can represent the average particle size of molecular sieve microparticles. The molecular sieve microparticle is the molecular sieve geometry with a certain shape and a size smaller than 50 μm, which retains the boundary (FIG. 10A) of growth shape of the original molecular sieve.

D90 refers to the particle size corresponding to the cumulative particle size distribution percentage of the molecular sieve microparticles on the surface of the hemostatic compound reaching 90%. Its physical meaning is that the molecular sieve microparticles with a particle size larger than it account for 10%, and the molecular sieve microparticles with a particle size smaller than it account for 90%.

There is a complete and uniform growth surface around the molecular sieve microparticles from traditional solution growth method of molecular sieve microparticles (FIG. 14). Different from the traditional solution growth method of molecular sieve microparticles, the growth-matched coupling is that the molecular sieve microparticles cooperate with the fiber surface to grow a tightly-coupled coupling interface with the fiber, as shown in FIGS. 11A-11B, so that the molecular sieve has a strong binding strength with the fiber.

The detection method for forming the growth-matched coupling is: the retention rate of the molecular sieve on the fiber is greater than or equal to 90% under ultrasonic condition for 20 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

In some embodiments, the detection method for forming the growth-matched coupling is: the retention rate of the molecular sieve on the fiber is greater than or equal to 90% under ultrasonic condition for 40 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

In some embodiments, the detection method for forming the growth-matched coupling is: the retention rate of the molecular sieve on the fiber is greater than or equal to 90% under ultrasonic condition for 60 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

In some embodiments, the molecular sieve nanoparticles are particles formed by molecular sieve growing in a nanometer-scale size (2 to 500 nm).

In some embodiments, the average size of the molecular sieve nanoparticles of outer surface is larger than the average size of the molecular sieve nanoparticles of inner surface.

In some embodiments, the particle diameter D90 of the molecular sieve is 0.1 to 30 μm, and the particle diameter D50 of the molecular sieve is 0.05 to 15 μm; preferably, the particle diameter D90 of the molecular sieve is 0.5 to 20 μm, and the particle diameter D50 of the molecular sieve is 0.25 to 10 μm; preferably, the particle diameter D90 of the molecular sieve is 1 to 15 μm, and the particle diameter D50 of the molecular sieve is 0.5 to 8 μm; more preferably, the particle diameter D90 of the molecular sieve is 5 to 10 μm, and the particle diameter D50 of the molecular sieve is 2.5 to 5 μm.

In some embodiments, the molecular sieve nanoparticles of outer surface are particles with corner angles.

In some embodiments, the molecular sieve nanoparticles of inner surface are particles without corner angles. The nanoparticles without corner angles make the inner surface of the molecular sieve match the fiber surface better, which is beneficial to the combination of the molecular sieve and the fiber.

In some embodiments, the average size of the molecular sieve nanoparticles of inner surface is 2 to 100 nm; preferably, the average size of the molecular sieve nanoparticles of inner surface is 10 to 60 nm.

In some embodiments, the average size of the molecular sieve nanoparticles of outer surface is 50 to 500 nm; preferably, the average size of the molecular sieve nanoparticles of outer surface is 100 to 300 nm.

In some embodiments, the non-planar surface is composed of any one or combination of non-planar curves or non-planar lines. For example, the non-planar surface is composed of non-planar curves. Preferably, the non-planar surface is a spherical surface, and the spherical surface increases the effective area of contact with a substance. The spherical surface is made up of non-planar curves. In another example, the non-planar surface may be composed of non-planar curves and non-planar lines. In some embodiments, the non-planar line may be a polygonal line.

In some embodiments, the molecular sieve is a mesoporous molecular sieve.

In some embodiments, the molecular sieve is independently dispersed on the fiber surface, that is, the molecular sieve does not aggregate on the fiber surface. And the molecular sieve is independently dispersed on the fiber surface so that the fiber maintains the original physical properties of flexibility and elasticity. The independent dispersion means that each molecular sieve microparticle has its own independent boundary; as shown in FIG. 10A, the boundary of each molecular sieve microparticle is clearly visible.

As an example, the aggregation of molecular sieves on the fiber surface (e.g. molecular sieves are distributed on the fiber surface in an agglomerated or lumpy structure) refer to the partial or full overlap of the molecular sieve microparticles and their nearest neighbor molecular sieve microparticles in space; that is, the minimum distance between the molecular sieve microparticles is less than one half of the sum of the particle size of the two molecular sieve microparticles, as shown in FIG. 20A, $d < r_1 + r_2$.

Different from the aggregation of molecular sieve on the fiber surface, the independent dispersion means that the molecular sieve microparticles are dispersed on the fiber surface with a gap between each other, and the independent dispersion means the minimum distance between the molecular sieve microparticles and the nearest molecular sieve microparticles is greater than or equal to one half of the sum of the particle sizes of the two molecular sieve microparticles, as shown in FIG. 20B, $d \geq r_1 + r_2$, which indicates the boundary between the adjacent molecular sieve microparticles.

In some embodiments, the content of the molecular sieve accounts for 0.05 to 80 wt % of the hemostatic compound; preferably, the content of the molecular sieve accounts for 1 to 50 wt % of the hemostatic compound; preferably, the content of the molecular sieve accounts for 5 to 35 wt % of the hemostatic compound; preferably, the content of the molecular sieve accounts for 10 to 25 wt % of the hemostatic compound; more preferably, the content of the molecular sieve accounts for 15 to 20 wt % of the hemostatic compound.

In some embodiments, the molecular sieve is selected from any one or more of X-type molecular sieve, Y-type molecular sieve, A-type molecular sieve, ZSM-5 molecular sieve, chabazite, β-molecular sieve, mordenite, L-type molecular sieve, P-type molecular sieve, merlinoite, $AlPO_4$-5 molecular sieve, $AlPO_4$-11 molecular sieve, SAPO-31 molecular sieve, SAPO-34 molecular sieve, SAPO-11 molecular sieve, BAC-1 molecular sieve, BAC-3 molecular sieve, and BAC-10 molecular sieve.

In some embodiments, the molecular sieve is a molecular sieve after metal ion exchange.

Further, the metal ion is selected from any one or more of strontium ion, calcium ion, magnesium ion, silver ion, zinc ion, barium ion, potassium ion, ammonium ion, and copper ion.

In some embodiments, the fiber is a polymer containing hydroxyl groups in a repeating unit.

Further, the fiber is selected from any one or more of silk fiber, chitin fiber, rayon fiber, acetate fiber, carboxymethyl cellulose, bamboo fiber, cotton fiber, linen fiber, wool, wood fiber, lactide polymer fiber, glycolide polymer fiber, polyester fiber (abbreviated as PET), polyamide fiber (abbreviated as PA), polypropylene fiber (abbreviated as PP), polyethylene fiber (abbreviated as PE), polyvinyl chloride fiber (abbreviated as PVC), polyacrylonitrile fiber (abbreviated as acrylic fiber, artificial wool), and viscose fiber.

Further, the polyester fiber refers to a polyester obtained by polycondensation of a monomer having both a hydroxyl group and a carboxyl group, or a polyester obtained by polycondensation of an aliphatic dibasic acid and an aliphatic diol, or polyester or copolyester made from aliphatic lactone through ring-opening polymerization, and the molecular weight of the aliphatic polyester is 50,000 to 250,000. The polyester obtained by polycondensation of a monomer having both a hydroxyl group and a carboxyl group is a polylactic acid obtained by direct polycondensation of lactic acid; the polyester obtained by polycondensation of an aliphatic dibasic acid and an aliphatic diol is polybutylene succinate, polyhexanediol sebacate, polyethylene glycol succinate or polyhexyl succinate; polyester produced from ring-opening polymerization of aliphatic lactones is polylactic acid obtained by ring-opening polymerization of lactide, and polycaprolactone obtained by ring-opening polymerization of caprolactone; copolyester is poly(D,L-lactide-co-glycolide).

Further, the polyamide fiber refers to polyhexamethylene adipamide obtained by polycondensation of diamine and diacid, and the chemical structure formula of its long chain molecule is: H—[HN$(CH_2)_x$NHCO$(CH_2)_y$CO]n-OH; or obtained by polycondensation or ring-opening polymerization of caprolactam, the chemical structural formula of its long chain molecule is: H—[NH$(CH_2)_x$CO]n-OH.

In some embodiments, the hemostatic compound is prepared by an in-situ growth method.

Further, the in-situ growth method includes the following steps:

(i) prepare a molecular sieve precursor solution and mix it with the fiber;

(ii) the mixture of fiber and molecular sieve precursor solution in step (i) is processed with heat treatment to obtain a hemostatic compound.

In some embodiments, the molecular sieve precursor solution does not include a templating agent.

In some embodiments, in the step (ii), the temperature of the heat treatment is 60 to 220° C., and the time of heat treatment is 4 to 240 h.

In some embodiments, in the step (i), mass ratio of the fiber to the molecular sieve precursor solution is 1:0.5 to 1:1000; preferably, in the step (i), mass ratio of the fiber to the molecular sieve precursor solution is 1:0.8 to 1:100; preferably, in the step (i), mass ratio of the fiber to the molecular sieve precursor solution is 1:1 to 1:50; preferably, in the step (i), mass ratio of the fiber to the molecular sieve precursor solution is 1:1.5 to 1:20; preferably, in the step (i), mass ratio of the fiber to the molecular sieve precursor solution in is 1:2 to 1:10; more preferably, in the step (i), mass ratio of the fiber to the molecular sieve precursor solution is 1:2 to 1:5.

In view of the shortcomings of the prior art, the second technical problem to be solved by the present disclosure is to provide a method for synthesizing a hemostatic compound by using fibers as a scaffold for nucleation and crystal growth of molecular sieve, and a new template-free in-situ growth method, without adding an adhesive. This method has the characteristics of low cost, simple process and environmental friendliness.

The present disclosure adopts the following technical solutions:

The present disclosure provides a preparation method for a hemostatic compound as described above, including the following steps:

(i) prepare a molecular sieve precursor solution and mix it with the fiber;

(ii) the mixture of fiber and molecular sieve precursor solution in step (i) is processed with heat treatment to obtain a hemostatic compound.

In some embodiments, the molecular sieve precursor solution does not include a templating agent.

In some embodiments, in the step (ii), the temperature of the heat treatment is 60 to 220° C., and the time of heat treatment is 4 to 240 h.

In some embodiments, in the step (i), mass ratio of the fiber to the molecular sieve precursor solution is 1:0.5 to 1:1000; preferably, in the step (i), mass ratio of the fiber to the molecular sieve precursor solution is 1:0.8 to 1:100; preferably, in the step (i), mass ratio of the fiber to the molecular sieve precursor solution is 1:1 to 1:50; preferably, in the step (i), mass ratio of the fiber to the molecular sieve precursor solution is 1:1.5 to 1:20; preferably, in the step (i), mass ratio of the fiber to the molecular sieve precursor solution in is 1:2 to 1:10; more preferably, in the step (i), mass ratio of the fiber to the molecular sieve precursor solution is 1:2 to 1:5.

In some embodiments, the molecular sieve is a mesoporous molecular sieve.

In some embodiments, the adhesive content of the contact surface between the molecular sieve and the fiber is zero. The surface of molecular sieve contacted with the fiber is inner surface, and the inner surface is a rough planar surface matched with the fiber surface, and growth-matched coupling is formed between the molecular sieve and the fiber on the inner surface of the molecular sieve. The surface of molecular sieve uncontacted with the fiber is outer surface, and the outer surface is non-planar surface. Both the inner surface and outer surface are composed of molecular sieve nanoparticles.

In some embodiments, the detection method for forming the growth-matched coupling is: the retention rate of the molecular sieve on the fiber is greater than or equal to 90% under ultrasonic condition for 20 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

In some embodiments, the detection method for forming the growth-matched coupling is: the retention rate of the molecular sieve on the fiber is greater than or equal to 90% under ultrasonic condition for 40 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

In some embodiments, the detection method for forming the growth-matched coupling is: the retention rate of the molecular sieve on the fiber is greater than or equal to 90% under ultrasonic condition for 60 minutes or more; preferably, the retention rate is greater than or equal to 95%; more preferably, the retention rate is 100%, that is, the molecular sieve has a strong binding strength with the fiber, and the molecular sieve does not easily fall off the fiber surface.

The molecular sieve nanoparticles are particles formed by molecular sieve growing in a nanometer-scale size (2 to 500 nm).

In some embodiments, the average size of the molecular sieve nanoparticles of outer surface is larger than the average size of the molecular sieve nanoparticles of inner surface.

In some embodiments, the particle diameter D90 of the molecular sieve is 0.1 to 30 μm, and the particle diameter D50 of the molecular sieve is 0.05 to 15 μm; preferably, the particle diameter D90 of the molecular sieve is 0.5 to 20 μm, and the particle diameter D50 of the molecular sieve is 0.25 to 10 μm; preferably, the particle diameter D90 of the molecular sieve is 1 to 15 μm, and the particle diameter D50 of the molecular sieve is 0.5 to 8 μm; more preferably, the particle diameter D90 of the molecular sieve is 5 to 10 μm, and the particle diameter D50 of the molecular sieve is 2.5 to 5 μm.

In some embodiments, the molecular sieve nanoparticles of outer surface are particles with corner angles.

In some embodiments, the molecular sieve nanoparticles of inner surface are particles without corner angles. The nanoparticles without corner angles make the inner surface of the molecular sieve match the fiber surface better, which is beneficial to the combination of the molecular sieve and the fiber.

In some embodiments, the average size of the molecular sieve nanoparticles of inner surface is 2 to 100 nm; preferably, the average size of the molecular sieve nanoparticles of inner surface is 10 to 60 nm.

In some embodiments, the average size of the molecular sieve nanoparticles of outer surface is 50 to 500 nm; preferably, the average size of the molecular sieve nanoparticles of outer surface is 100 to 300 nm.

In some embodiments, the non-planar surface is composed of any one or combination of non-planar curves or a non-planar lines. For example, the non-planar surface is made up of non-planar curves. Preferably, the non-planar surface is a spherical surface, and the spherical surface increases the effective area of contact with a substance. The spherical surface is made up of non-planar curves. In another example, the non-planar surface may be composed of non-planar curves and non-planar lines. In some embodiments, the non-planar line may be a polygonal line.

In some embodiments, the content of the molecular sieve accounts for 0.05 to 80 wt % of the hemostatic compound; preferably, the content of the molecular sieve accounts for 1 to 50 wt % of the hemostatic compound; preferably, the content of the molecular sieve accounts for 5 to 35 wt % of the hemostatic compound; preferably, the content of the molecular sieve accounts for 10 to 25 wt % of the hemostatic compound; more preferably, the content of the molecular sieve accounts for 15 to 20 wt % of the hemostatic compound.

In some embodiments, the molecular sieve is selected from any one or more of X-type molecular sieve, Y-type molecular sieve, A-type molecular sieve, ZSM-5 molecular sieve, chabazite, β-molecular sieve, mordenite, L-type molecular sieve, P-type molecular sieve, merlinoite, $AlPO_4$-5 molecular sieve, $AlPO_4$-11 molecular sieve, SAPO-31 molecular sieve, SAPO-34 molecular sieve, SAPO-11 molecular sieve, BAC-1 molecular sieve, BAC-3 molecular sieve, and BAC-10 molecular sieve.

In some embodiments, the fiber is a polymer containing hydroxyl groups in a repeating unit.

Further, the fiber is selected from any one or more of silk fiber, chitin fiber, rayon fiber, acetate fiber, carboxymethyl cellulose, bamboo fiber, cotton fiber, linen fiber, wool, wood fiber, lactide polymer fiber, glycolide polymer fiber, polyester fiber (abbreviated as PET), polyamide fiber (abbreviated as PA), polypropylene fiber (abbreviated as PP), polyethylene fiber (abbreviated as PE), polyvinyl chloride fiber (abbreviated as PVC), polyacrylonitrile fiber (abbreviated as acrylic fiber, artificial wool), and viscose fiber.

A third object of the present disclosure is to provide a composite material, the composite material comprising any one of the forms of hemostatic compound as described above or a hemostatic compound prepared by any of the forms of preparation methods as described above.

In some embodiments, the composite material is a hemostatic textile.

Further, the hemostatic textile is selected from any one or more of a hemostatic bandage, a hemostatic gauze, a hemostatic cloth, a hemostatic clothing, a hemostatic cotton, a hemostatic suture, a hemostatic paper, and a hemostatic band-aid.

Further, the hemostatic clothing is a material worn on the human body for protection or decoration.

Further, the hemostatic clothing is selected from any one or more of hemostatic underwear, hemostatic vest, hemostatic cap, and hemostatic pants.

The beneficial effects of the present disclosure are:

1. For the first time, a novel hemostatic compound is prepared by the present disclosure. Without the addition of an adhesive, the inner surface of the molecular sieve is a planar surface that matches the fiber surface. The molecular sieve and the fiber have a strong binding strength to form the hemostatic compound. The molecular sieve on the fiber surface has a high effective specific surface area and excellent substance exchange capacity. It speeds up the coagulation reaction and plays a role of rapid coagulation, and eliminates the problem that the molecular sieve easily falls off the fiber surface, eradicates the problem that the hemostatic compound easily loses the hemostatic effect, solves the problem that some detachable molecular sieves will adhere to the wound and cause thrombosis, and finally improves the performance and safety of the hemostatic compound.

2. The present disclosure provides a method for synthesizing a hemostatic compound by using fibers as a scaffold for nucleation and crystal growth of molecular sieve, and a template-free in-situ growth method. This method has the characteristics of low cost, simple process and environmental friendliness, and achieves good technical effects.

3. The present disclosure provides a hemostatic compound that is superior to granular or powdery molecular sieve materials, and solves the problems of molecular sieve absorbing water and exothermic heat. In addition, the hemostatic compound also has the following advantages: (i) the wound surface after hemostasis is easy to clean up and convenient for post-processing by professionals; (ii) the hemostatic compound can be tailored for wound size and practical needs; (iii) the wound after hemostasis is dry and heals well after treated with the hemostatic compound.

BRIEF DESCRIPTION OF THE DRAWINGS

FIGS. 20A-20B are schematic diagram of the positional relationship between two adjacent molecular sieve microparticles on the fiber surface of the hemostatic compound; wherein, FIG. 20A is the aggregation of molecular sieve on the fiber surface in the composite in the prior art, and FIG. 20B is the molecular sieve is independently dispersed on the fiber surface in the composite in the present disclosure.

DETAILED DESCRIPTION OF THE DISCLOSURE

Figure 1:
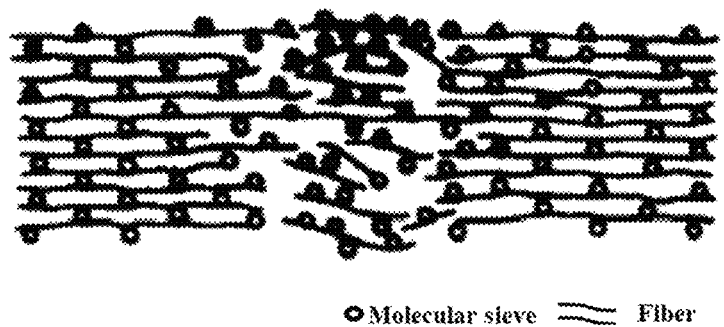
FIG. 1 is a schematic diagram showing the destruction of a fiber structure caused by pretreatment of fiber in the prior art.
Figure 2:
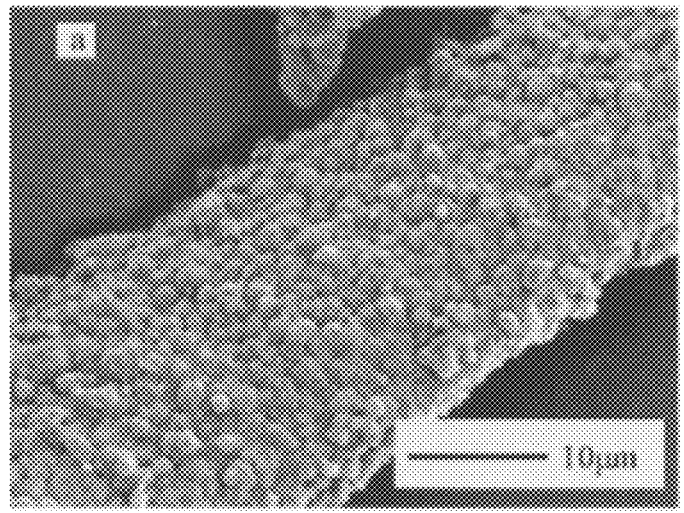
FIG. 2 is a scanning electron microscope image of a molecular sieve/fiber composite after pretreatment of fiber in the prior art, in which the molecular sieve is wrapped on the fiber surface in an agglomerated form (Journal of Porous Materials, 1996, 3 (3): 143-150).
Figure 3:
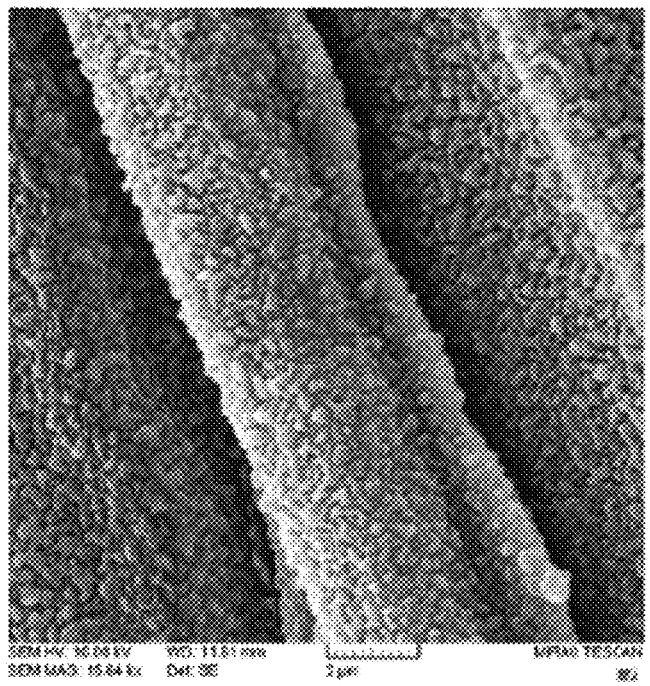
FIG. 3 is a scanning electron microscope image of a molecular sieve/fiber composite after pretreatment of fiber in the prior art, in which the molecular sieve is wrapped on the fiber surface in an agglomerated or lumpy form (Cellulose, 2015, 22 (3): 1813-1827).
Figure 4:
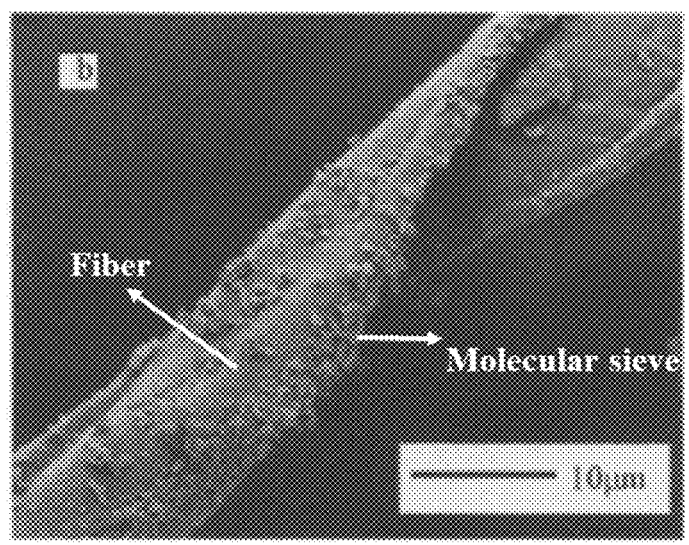
FIG. 4 is a scanning electron microscope image of a molecular sieve/fiber composite after pretreatment of fiber in the prior art, in which the molecular sieve is partially agglomerated and unevenly distributed on the fiber surface (Journal of Porous Materials, 1996, 3 (3): 143-150).
Figure 5:
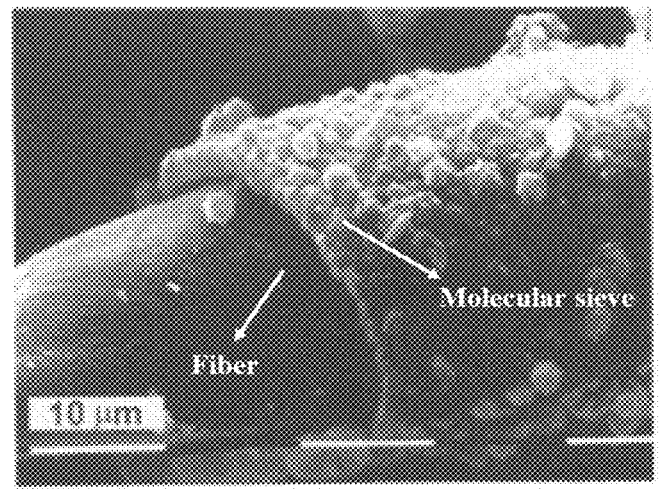
FIG. 5 is a scanning electron microscope image of a molecular sieve/fiber composite after pretreatment of fiber the prior art, in which a gap exists between the fiber and the molecular sieve (Journal of Porous Materials, 1996, 3 (3): 143-150).
Figure 6:
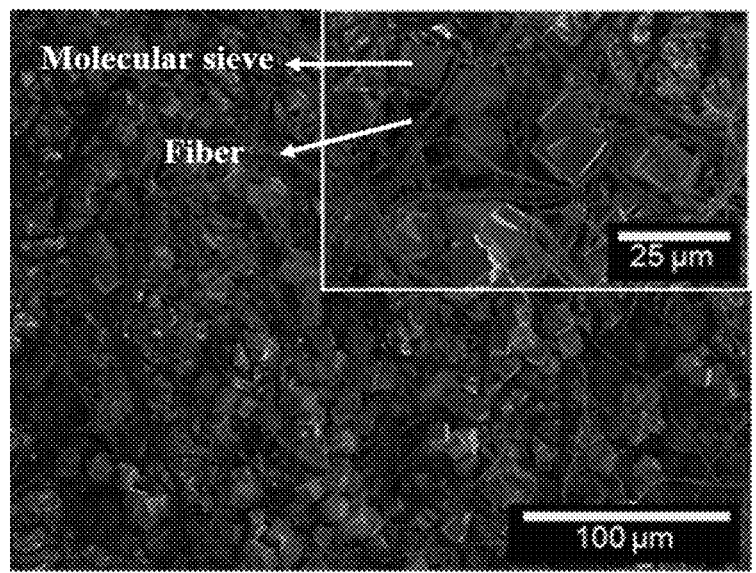
FIG. 6 is a scanning electron microscope image of a Na-LTA molecular sieve/nanocellulose fiber composite bonded by polydiallyl dimethyl ammonium chloride in the prior art (ACS Appl. Mater. Interfaces 2016, 8, 3032-3040).
Figure 7:
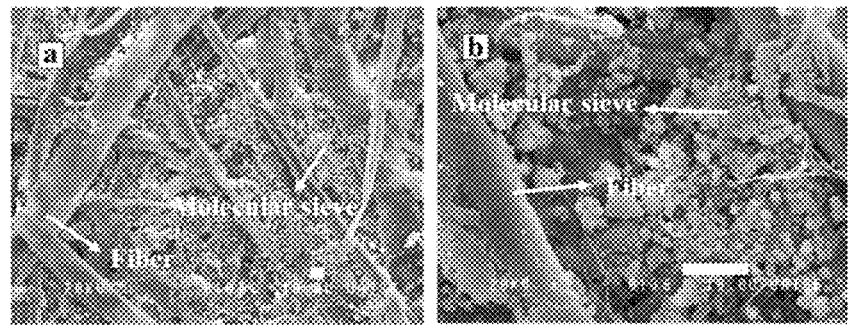
FIG. 7 is a scanning electron microscope image of a NaY molecular sieve/fiber composite bonded by a cationic and anionic polymer adhesive in the prior art (Microporous & Mesoporous Materials, 2011, 145 (1-3): 51-58).
Figure 8:
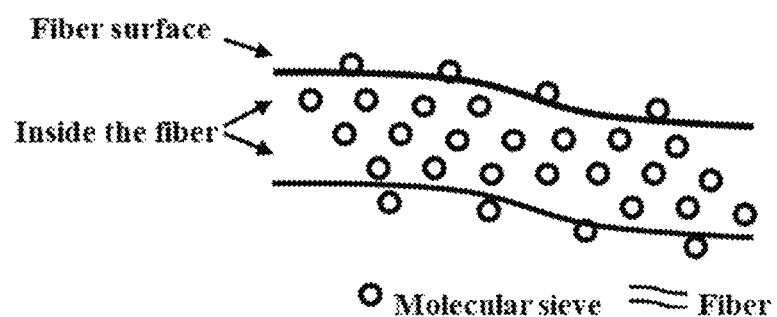
FIG. 8 is a schematic diagram of a molecular sieve/fiber composite prepared by blend spinning in the prior art.
Figure 9:
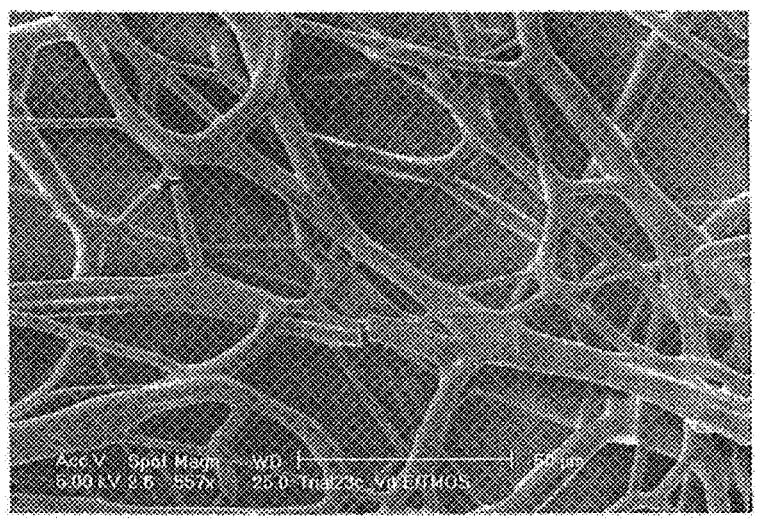
FIG. 9 is a schematic diagram of molecular sieve/fiber composite prepared by electrospun in the prior art (U.S. Pat. No. 7,739,452B2).

The present disclosure is further described below with reference to the drawings and embodiments.

The "degree of ion exchange" is the ion exchange capacity of the compensation cations outside the molecular sieve framework and cations in the solution. The method for detecting the ion exchange capacity is: immersing hemostatic compounds in a 5M concentration strontium chloride, calcium chloride or magnesium chloride solution at room temperature for 12 hours to obtain a hemostatic compound after ion exchange, and measuring the degree of strontium ion, calcium ion or magnesium ion exchange of the molecular sieves of hemostatic compounds after ion exchange.

"Effective specific surface area of molecular sieve" shows the specific surface area of the molecular sieve on the fiber surface in the hemostatic compound. The detection method of the effective specific surface area of the molecular sieve: the specific surface area of the hemostatic compound is analyzed by nitrogen isothermal adsorption and desorption, and the effective specific surface area of the molecular sieve=the specific surface area of the hemostatic compound−the specific surface area of the fiber.

Detection method of "content of molecular sieve on fiber surface": the mass fraction of molecular sieve on the fiber is analyzed using a thermogravimetric analyzer.

The detection method of "uniform distribution of molecular sieves on the fiber surface" is: randomly taking n samples of the hemostatic compound at different locations and analyzing the content of the molecular sieve on the fiber surface, where n is a positive integer greater than or equal to 8. The coefficient of variance is also called the "standard deviation rate", which is the ratio of the standard deviation to the mean multiplied by 100%. The coefficient of variation is an absolute value that reflects the degree of dispersion of the data. The smaller the value of the coefficient of variation, the smaller the degree of dispersion of the data, indicating that the smaller the difference in the content of molecular sieves on the fiber surface, the more uniform the distribution of molecular sieves on the fiber surface. The coefficient of variation of the content of the molecular sieves in the n samples is ≤15%, indicating that the molecular sieves are uniformly distributed on the fiber surface. Preferably, the coefficient of variation of the content of the molecular sieves is ≤10%, indicating that the molecular sieves are uniformly distributed on the fiber surface. Preferably, the coefficient of variation of the content of the molecular sieves is ≤5%, indicating that the molecular sieves are uniformly distributed on the fiber surface. Preferably, the coefficient of variation of the content of the molecular sieves is ≤2%, indicating that the molecular sieves are uniformly distributed on the fiber surface. Preferably, the coefficient of variation of the content of the molecular sieves is ≤1%, indicating that the molecular sieves are uniformly distributed on the fiber surface. Preferably, the coefficient of variation of the content of the molecular sieves is ≤0.5%, indicating that the molecular sieves are uniformly distributed on the fiber surface. Preferably, the coefficient of variation of the content of the molecular sieves is ≤0.2%, indicating that the molecular sieves are uniformly distributed on the fiber surface.

The detection methods of D50 and D90 are: using scanning electron microscope to observe the molecular sieve microparticles on the surface of the hemostatic compound, and carrying out statistical analysis of particle size. D50 refers to the particle size corresponding to the cumulative particle size distribution percentage of the molecular sieve microparticles reaching 50%. D90 refers to the particle size corresponding to the cumulative particle size distribution percentage of the molecular sieve microparticles reaching 90%.

The detection method of the binding strength between the molecular sieve and the fiber is: putting hemostatic compound in deionized water under ultrasonic condition for 20 min or more, and analyzing the content of the molecular sieve on the fiber surface by using a thermogravimetric analyzer. The retention rate on the fiber, the retention rate=(content of the molecular sieve on the fiber surface before the ultrasound−content of the molecular sieve on the fiber surface after the ultrasound)×100%/content of the molecular sieve on the fiber surface before the ultrasound. If the retention rate is greater than or equal to 90%, it indicates that molecular sieve and fiber form a growth-matched coupling, and molecular sieve is firmly bonded to fiber.

Detection method of hemostatic function of hemostatic compound: The hemostatic function of hemostatic compound is evaluated by using a rabbit femoral artery lethal model. The specific steps are as follows: (1) before the experiment, white rabbits were anesthetized with sodium pentobarbital intravenously (45 mg/kg); their limbs and head were fixed, and supine on the experimental table; part of the hair was removed to expose the right groin of the hind limb. (2) Then, the femoral skin and muscle were cut longitudinally to expose the femoral artery, and the femoral artery was partially cut off (about half of the circumference). After the femoral artery was allowed to squirt freely for 30 seconds, the blood at the wound was cleaned with cotton gauze, and then the hemostatic compound was quickly pressed to the wound. After pressing for 60 seconds, the hemostatic compound is lifted up slightly every 10 seconds to observe the coagulation of the injured part and the coagulation time is recorded. Infrared thermometers are used to detect changes in wound temperature (before and after using hemostatic compound). (3) After hemostasis, observe the wound and suture the wound. The survival of the animals is observed for 2 hours after hemostasis. The survival rate=(total number of experimental white rabbits-number of deaths of white rabbits observed for 2 hours after hemostasis)×100%/total number of experimental white rabbits, wherein the number of experimental white rabbits in each group is n, n is a positive integer greater than or equal to 6. (4) The difference in weight of the hemostatic compound before and after use was recorded as the amount of blood loss during wound hemostasis.

Example 1

The preparation method of the Y-type molecular sieve/cotton fiber hemostatic compound of the present disclosure includes the following steps:

(i) A molecular sieve precursor solution was prepared, and a starting material was composed of $10Na_2O:Al_2O_3:9SiO_2:200H_2O$ in a molar ratio to synthesize a molecular sieve precursor solution. The molecular sieve precursor solution was mixed with cotton fiber, and the mass ratio of the cotton fiber and the molecular sieve precursor solution is 1:20.

(ii) The cotton fiber and the homogeneously-mixed molecular sieve precursor solution were heat-treated at 100° C. for 24 h to obtain a Y-type molecular sieve/cotton fiber hemostatic compound.

Ten samples of the prepared Y-type molecular sieve/cotton fiber hemostatic compound were randomly taken at different locations, and the content of the Y-type molecular sieve on the fiber surface was analyzed by a thermogravimetric analyzer. The content of molecular sieve on the fiber in the ten samples was 25 wt %, 24.9 wt %, 25.1 wt %, 25.2 wt %, 25 wt %, 25 wt %, 24.9 wt %, 25 wt %, 25.1 wt %, 24.9 wt %. The average content of molecular sieves on the fibers in the ten samples was 25 wt %, the standard deviation of the samples is 0.1 wt %, and the coefficient of variation is 0.4%, which indicates that the Y-type molecular sieve is uniformly distributed on the fiber surface.

Figure 10A:
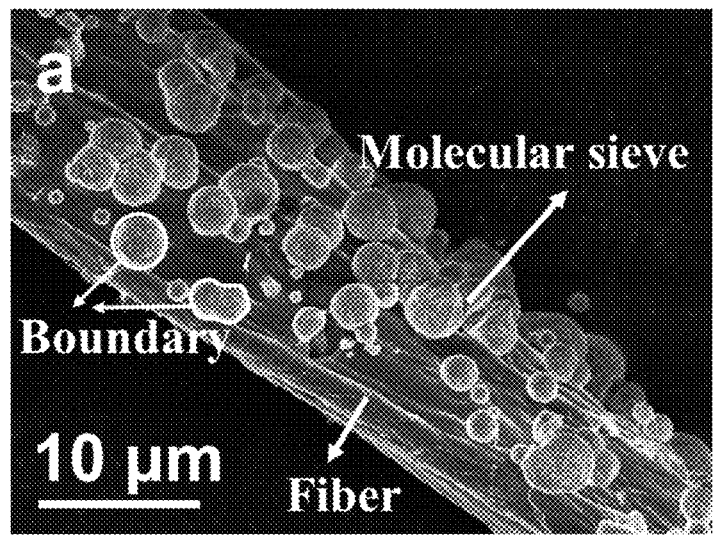
FIG. 10A is a scanning electron microscope image of a hemostatic compound according to the present disclosure (Bar=10 μm) (test parameter SU80100 3.0 kV; 9.9 mm).
Figure 10B:
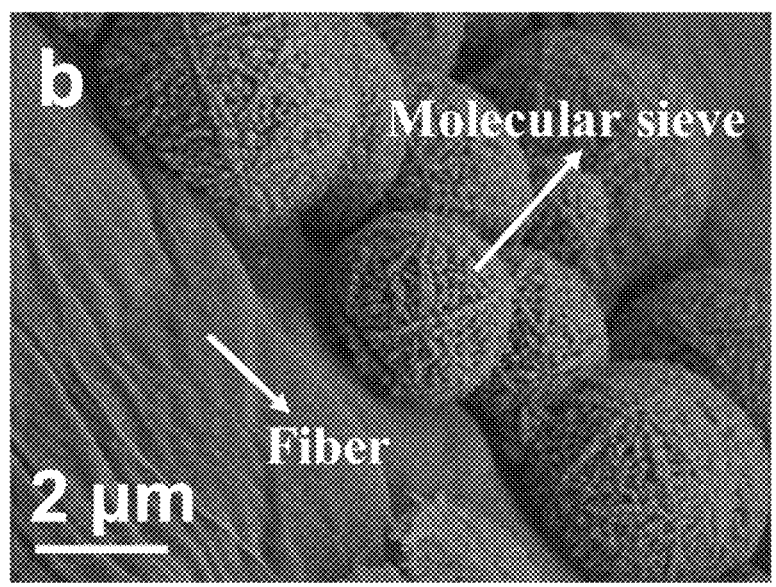
FIG. 10B is a scanning electron microscope image of the hemostatic compound according to the present disclosure (Bar=2 μm) (test parameter SU80100 3.0 kV; 9.9 mm).
Figure 11A:
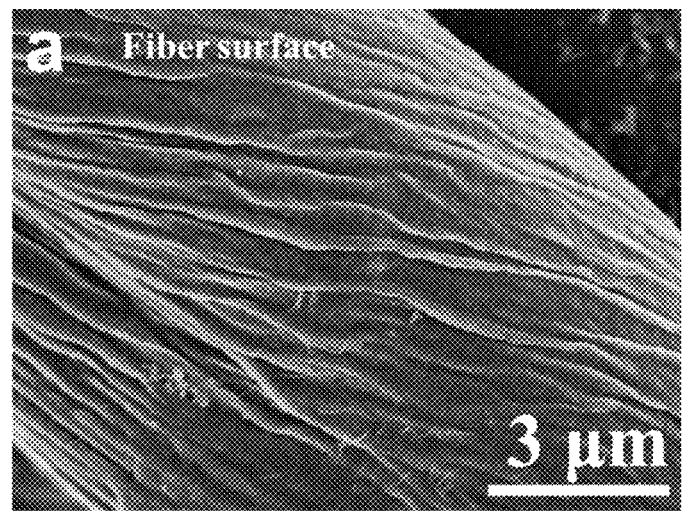
FIG. 11A is a scanning electron microscope image of fibers in the hemostatic compound before the fibers are bonded with the molecular sieve (test parameter SU80100 3.0 kV; 9.9 mm).
Figure 11B:
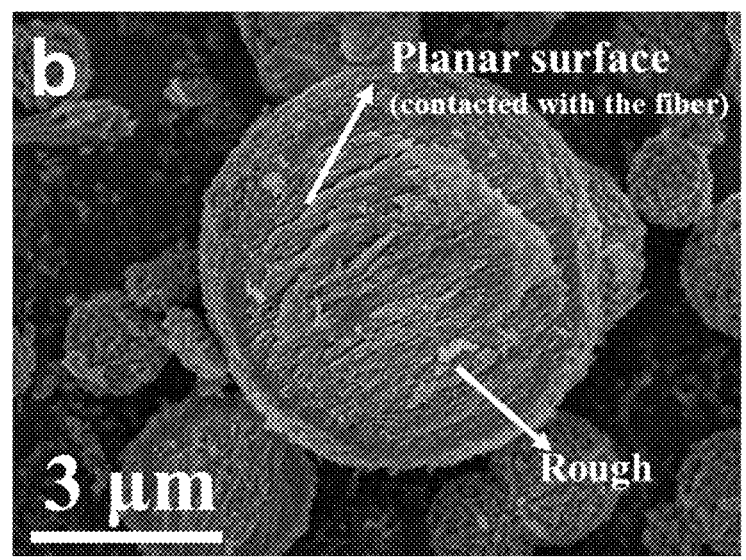
FIG. 11B is a scanning electron microscope image of molecular sieves in the hemostatic compound after the fibers are removed from the hemostatic compound (test parameter SU80100 3.0 kV; 9.9 mm).
Figure 12:
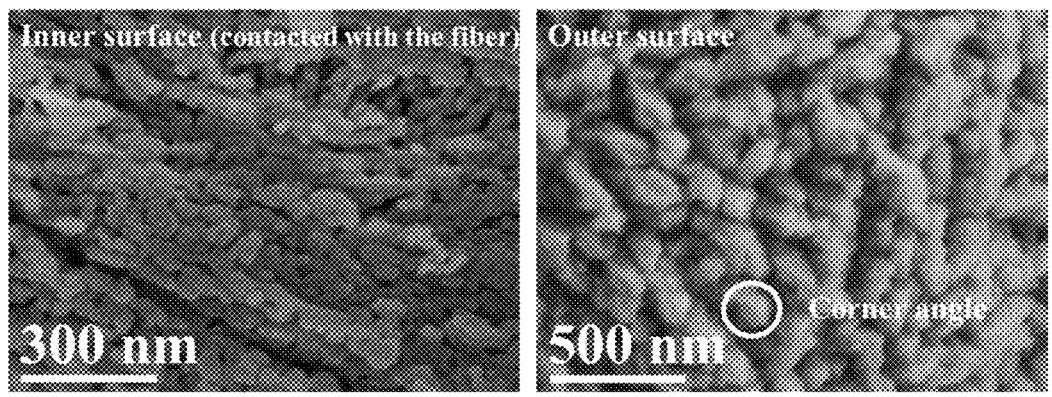
FIG. 12 shows scanning electron microscope images of the inner surface (the contact surface between the molecular sieve and the fiber)(Bar=300 nm) and the outer surface (Bar=500 nm) of the molecular sieve of the hemostatic compound according to the present disclosure (test parameter SU80100 5.0 kV; 9.9 mm).
Figure 13:
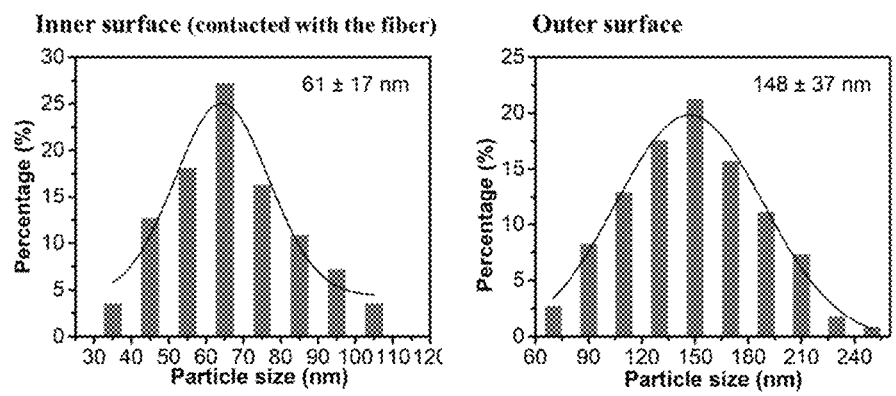
FIG. 13 shows statistical distribution diagrams of particle sizes of nanoparticles on the inner surface and the outer surface of the molecular sieve of the hemostatic compound according to the present disclosure.

The prepared Y-type molecular sieve/cotton fiber hemostatic compound was observed with a scanning electron microscope. Hemispherical molecular sieves with an average particle size of 5 μm are independently dispersed on the fiber surface, as shown in FIGS. 10A-10B. The molecular sieves microparticles of the molecular sieve/fiber composite are observed with a scanning electron microscope, and are performed statistical analysis of particle size to obtain a particle diameter D90 value of 25 μm and a particle diameter D50 value of 5 μm. The molecular sieves are obtained after removing the fibers by calcination. The inner surface of the molecular sieves in contact with the fiber is planar surface (caused by tight binding with the fiber), and the outer surface is spherical surface. The planar surface of the inner surface of the molecular sieves is a rough surface, as shown in FIGS. 11A-11B. The outer surface of the molecular sieve is composed of nanoparticles with corner angles, and the inner surface (the contact surface with the fiber) is composed of nanoparticles without corner angles (FIG. 12). The nanoparticles without corner angles make the inner surface of the molecular sieve match the fiber surface better, which is beneficial to the combination of the molecular sieve and the fiber. The average size of nanoparticles of the inner surface (61 nm) is significantly smaller than that of the outer surface (148 nm), and small-sized particles are more conducive to binding with fibers tightly (FIG. 13). The detection method of the binding strength between the molecular sieve and the fiber: the hemostatic compound is under ultrasonic condition in deionized water for 20 min, and the content of the Y-type molecular sieves on the fiber surface is analyzed by using a thermogravimetric analyzer. It is found that the content of the molecular sieve on the fiber surface is the same before and after ultrasonic condition. It shows that the retention rate of molecular sieve on the fiber is 100%, which indicates that the growth-matched coupling is formed between the molecular sieve and the fiber. The molecular sieve in the Y-type molecular sieve/cotton fiber hemostatic compound was analyzed by nitrogen isothermal adsorption and desorption, and a hysteresis loop was found in the isothermal adsorption curve, indicating that the molecular sieve has a mesoporous structure. Using the method for detecting the effective specific surface area of the molecular sieve as described above, the effective specific surface area of the molecular sieve in the Y-type molecular sieve/cotton fiber hemostatic compound prepared in this embodiment was measured to be 490 $m^2g^{-1}$. Using the method for detecting the ion exchange capacity of the molecular sieve in the Y-type molecular sieve/cotton fiber hemostatic compound, the degree of calcium ion exchange is 99.9%, the degree of magnesium ion exchange is 97%, and the degree of strontium ion exchange is 90%.

Comparative Example 1

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

The effective specific surface area of the Y-type molecular sieve was 490 $m^2g^{-1}$, the degree of calcium ion exchange was 99.9%, the degree of magnesium ion exchange was 97%, and the degree of strontium ion exchange was 90%.

Figure 14:
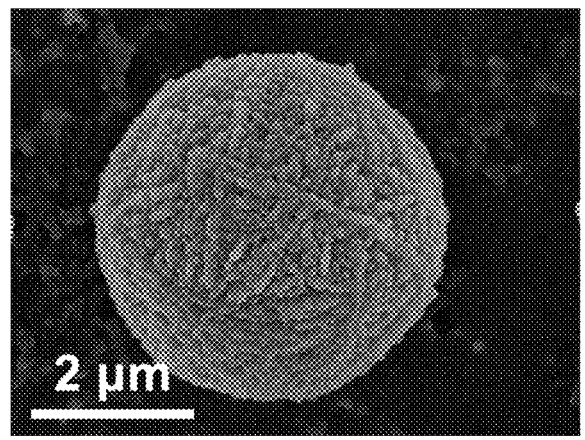
FIG. 14 is a scanning electron microscope image of a molecular sieve according to Comparative Example 1 (test parameter SU80100 5.0 kV; 9.9 mm).

The effective specific surface area and ion exchange capacity of the above Y-type molecular sieve are used as reference values to evaluate the performance of the molecular sieve to the fiber surface in the Comparative Examples described below. The difference between this Comparative Example 1 and Example 1 is that only the Y-type molecular sieve is synthesized without adding fibers (the traditional solution growth method). Using a scanning electron microscope (FIG. 14), the synthesized molecular sieve is a complete microsphere composed of nanoparticles, and there is no rough planar surface (inner surface) in contact with the fibers compared with Example 1.

Comparative Example 2

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) The above Y-type molecular sieve was added with deionized water to uniformly disperse the Y-type molecular sieve in an aqueous solution.

(4) Immerse the cotton fiber in the solution prepared in step (3) and soak for 30 min.

(5) Dry at 65° C. to obtain a Y-type molecular sieve/cotton fiber hemostatic complex (impregnation method).

Figure 15:
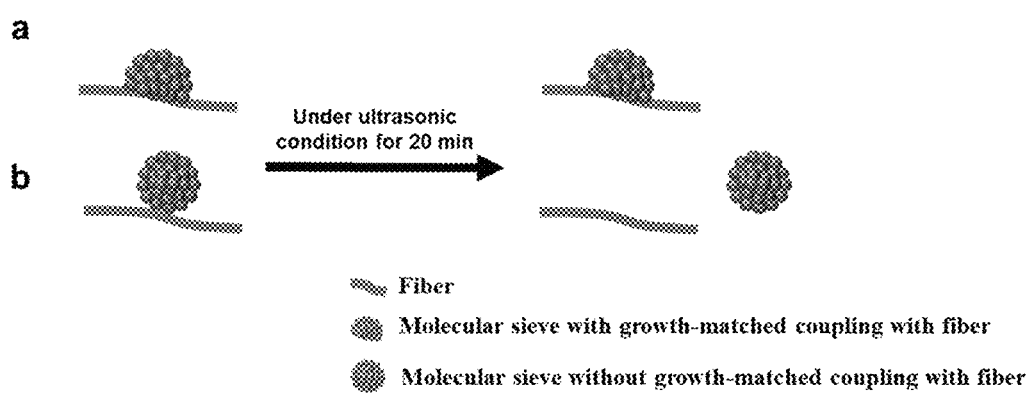
FIG. 15 is a schematic diagram showing the different binding strength of the molecular sieves and fibers of the molecular sieve/fiber compound according to the Comparative Example 2 of the present disclosure, with the influence of the growth-matched coupling between molecular sieves and fibers.
Figure 16:
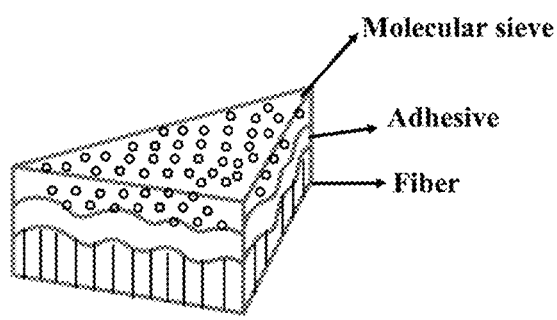
FIG. 16 is a schematic diagram of a molecular sieve/fiber composite bonded by an adhesive in the prior art. The fiber, the adhesive, and the molecular sieve form a sandwich-like structure, and the intermediate layer is an adhesive.

The difference between this Comparative Example and Example 1 is that only the Y-type molecular sieve is synthesized without adding fibers (the traditional solution growth method). Using a scanning electron microscope, the synthesized molecular sieve is a complete microsphere composed of nanoparticles, and there is no rough planar surface (inner surface) in contact with the fibers compared with Example 1. Therefore, there is no growth-matched coupling between the molecular sieve and the fiber surface (FIG. 15). The binding strength between the molecular sieve and the fiber was measured. The Y-type molecular sieve/cotton fiber hemostatic complex (impregnation method) was under the ultrasonic condition for 20 min, the retention rate of the molecular sieve on the fiber was 5%, indicating that the molecular sieve of Y-type molecular sieve/cotton fiber hemostatic complex (impregnation method) has a weak binding effect with the fiber, and the molecular sieve easily falls off (FIG. 15).

Comparative Example 3

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) The above Y-type molecular sieve was added with deionized water to uniformly disperse the Y-type molecular sieve in an aqueous solution.

(4) Spray the solution prepared in step (3) on cotton fibers (5) Dry at 65° C. to obtain a Y-type molecular sieve/cotton fiber hemostatic complex (spray method).

The difference between this Comparative Example and Example 1 is that the synthesized molecular sieve is sprayed onto cotton fibers. Using a scanning electron microscope, there is no rough planar surface (inner surface) in contact with the fibers compared with Example 1. Therefore, there is no growth-matched coupling between the molecular sieve and the fiber surface. The binding strength between the molecular sieve and the fiber was measured. The hemostatic complex was under the ultrasonic condition for 20 min, the retention rate of the molecular sieve on the fiber was 2%, indicating that the molecular sieve of Y-type molecular sieve/cotton fiber hemostatic complex (spray method) has a weak binding effect with the fiber, and the molecular sieve easily falls off.

Comparative Example 4

Refer to references for experimental steps (ACS Appl Mater Interfaces, 2016, 8(5):3032-3040).

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) The above Y-type molecular sieve was added with deionized water to uniformly disperse the Y-type molecular sieve in an aqueous solution.

(4) Cotton fibers were immersed in a 0.5 wt % polydiallyl dimethyl ammonium chloride (polyDADMAC) aqueous solution at 60° C. for 30 minutes to achieve adsorption of Y-type molecular sieves (polyDADMAC is an adhesive 1).

(5) Dry at 65° C. to obtain a Y-type molecular sieve/cotton fiber hemostatic complex (including adhesive 1).

The difference between this Comparative Example and Example 1 is that the synthesized molecular sieve is bonded to cotton fibers through an adhesive. After detection of scanning electron microscope, there is no rough planar surface (inner surface) in contact with the fiber, so there is no growth-matched coupling. The binding strength between the molecular sieve and the fiber was measured. The retention rate of the molecular sieve on the fiber was 50% under ultrasonic condition for 20 min, indicating that the molecular sieve has a weak binding strength with the fiber, and the molecular sieve in the Y-type molecular sieve/cotton fiber hemostatic complex (including adhesive 1) easily falls off. After detection of scanning electron microscope, the molecular sieve was unevenly distributed on the fiber surface, and there was agglomeration of the molecular sieve. After testing, with the addition of adhesive, the effective specific surface area of the molecular sieve became 320 $m^2g^{-1}$, the degree of calcium ion exchange became 75.9%, the degree of magnesium ion exchange became 57%, and the degree of strontium ion exchange became 50%. The complex material with added adhesive reduces the effective contact area between the molecular sieve and the reaction system, and reduces the ion exchange and pore substance exchange capacity of the molecular sieve.

Ten samples of the prepared Y-type molecular sieve/cotton fiber hemostatic complex (including adhesive 1) were randomly taken at different locations, and the content of the Y-type molecular sieve on the fiber surface was analyzed. The average content of molecular sieves on the fibers in the ten samples was 25 wt %, the standard deviation of the samples is 10 wt %, and the coefficient of variation is 40%, which indicates that the Y-type molecular sieve is unevenly distributed on the fiber surface.

Comparative Example 5

Refer to references for experimental steps (Colloids & Surfaces B Biointerfaces, 2018, 165:199).

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) The above Y-type molecular sieve was dispersed in a polymeric N-halamine precursor water/ethanol solution (polymeric N-halamine precursor is an adhesive 2).

(4) The solution prepared in the step (3) was sprayed on cotton fibers (5) Dry at 65° C. to obtain a Y-type molecular sieve/cotton fiber hemostatic complex (including adhesive 2).

The difference between this Comparative Example and Example 1 is that the molecular sieves with an adhesive were sprayed onto cotton fibers. After detection of scanning electron microscope, there is no rough planar surface (inner surface) in contact with the fiber, so there is no growth-matched coupling. The binding strength between the molecular sieve and the fiber was measured. The retention rate of the molecular sieve on the fiber was 41% under ultrasonic condition for 20 min, indicating that the molecular sieve has a weak binding strength with the fiber, and the molecular sieve in the Y-type molecular sieve/cotton fiber hemostatic complex (including adhesive 2) easily falls off. After detection of scanning electron microscope, the molecular sieve was unevenly distributed on the fiber surface, and there was agglomeration of the molecular sieve. After testing, with the addition of adhesive, the effective specific surface area of the molecular sieve became 256 $m^2g^{-1}$, the degree of calcium ion exchange became 65.9%, the degree of magnesium ion exchange became 47%, and the degree of strontium ion exchange became 42%. The complex material with added adhesive reduces the effective contact area between the molecular sieve and the reaction system, and reduces the ion exchange and pore substance exchange capacity of the molecular sieve.

Ten samples of the prepared Y-type molecular sieve/cotton fiber hemostatic complex (including adhesive 2) were randomly taken at different locations, and the content of the Y-type molecular sieve on the fiber surface was analyzed. The average content of molecular sieves on the fibers in the ten samples was 25 wt %, the standard deviation of the samples is 4 wt %, and the coefficient of variation is 16%, which indicates that the Y-type molecular sieve is unevenly distributed on the fiber surface.

Comparative Example 6

Refer to references for experimental steps (Key Engineering Materials, 2006, 317-318:777-780).

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) The Y-type molecular sieve sample was dispersed in a silica sol-based inorganic adhesive (adhesive 3) solution to obtain a slurry of a molecular sieve and adhesive mixture.

(4) The prepared slurry in the step (3) was coated on cotton fibers, and then kept at room temperature for 1 h, and then kept at 100° C. for 1 h. The fibers were completely dried to obtain a Y-type molecular sieve/cotton fiber hemostatic complex (including adhesive 3).

The difference between this Comparative Example and Example 1 is that the molecular sieves with a silica sol-based adhesive were coated on the cotton fibers. After detection of scanning electron microscope, there is no rough planar surface (inner surface) in contact with the fiber, so there is no growth-matched coupling. The binding strength between the molecular sieve and the fiber was measured. The retention rate of the molecular sieve on the fiber was 46% under ultrasonic condition for 20 min, indicating that the molecular sieve has a weak binding strength with the fiber, and the molecular sieve in the Y-type molecular sieve/cotton fiber hemostatic complex (including adhesive 3) easily falls off. After detection of scanning electron microscope, the molecular sieve was unevenly distributed on the fiber surface, and there was agglomeration of the molecular sieve. After testing, with the addition of adhesive, the effective specific surface area of the molecular sieve became 246 $m^2g^{-1}$, the degree of calcium ion exchange became 55.9%, the degree of magnesium ion exchange became 57%, and the degree of strontium ion exchange became 40%. The complex material with added adhesive reduces the effective contact area between the molecular sieve and the reaction system, and reduces the ion exchange and pore substance exchange capacity of the molecular sieve.

Ten samples of the prepared Y-type molecular sieve/cotton fiber hemostatic complex (including adhesive 3) were randomly taken at different locations, and the content of the Y-type molecular sieve on the fiber surface was analyzed. The average content of molecular sieves on the fibers in the ten samples was 25 wt %, the standard deviation of the samples is 8.5 wt %, and the coefficient of variation is 34%, which indicates that the Y-type molecular sieve is unevenly distributed on the fiber surface.

Comparative Example 7

Refer to references for experimental steps (Journal of Porous Materials, 1996, 3(3):143-150).

(1) The fibers were chemically pretreated. The fibers were first treated with ether for 20 minutes and sonicated in distilled water for 10 minutes.

(2) A molecular sieve precursor solution was prepared, and a starting material was composed of $7.5Na_2O:Al_2O_3:10SiO_2:230H_2O$ in a molar ratio to synthesize a molecular sieve precursor solution, followed by magnetic stirring for 1 h and standing at room temperature for 24 h. The molecular sieve precursor solution was mixed with pretreated cotton fibers.

(3) The pretreated cotton fiber and the homogeneously-mixed molecular sieve precursor solution were heat-treated at 100° C. for 6 h to obtain a Y-type molecular sieve/cotton fiber hemostatic complex (pretreatment of fiber).

The difference between this Comparative Example and Example 1 is that the fiber is pretreated, but the structure of the fiber itself is seriously damaged, which affects the characteristics such as the flexibility and elasticity of the fiber, and the fiber becomes brittle and hard. Therefore, the advantages of fiber as a carrier cannot be fully utilized. After detection by a scanning electron microscope, the molecular sieve was wrapped in the outer layer of the fiber, and there was still a gap between the fiber and the molecular sieve, indicating that this technology cannot tightly combine molecular sieve and fiber. Compared with Example 1, there is no rough planar surface (inner surface) in contact with the fiber, so there is no growth-matched coupling. The binding strength between the molecular sieve and the fiber was measured. The retention rate of the molecular sieve on the fiber was 63% under ultrasonic condition for 20 min, indicating that the molecular sieve has a weak binding strength with the fiber, and the molecular sieve in the Y-type molecular sieve/cotton fiber hemostatic complex (pretreatment of fiber) easily falls off. After testing, the agglomeration of molecular sieve makes the effective specific surface area of the molecular sieve to become 346 $m^2g^{-1}$, the degree of calcium ion exchange become 53%, the degree of magnesium ion exchange become 52%, and the degree of strontium ion exchange become 42%, which greatly reduces the effective contact area between the effective molecular sieve and the reaction system, and reduces the ion exchange and pore substance exchange capacity of the molecular sieve.

Ten samples of the prepared Y-type molecular sieve/cotton fiber hemostatic complex (pretreatment of fiber) were randomly taken at different locations, and the content of the Y-type molecular sieve on the fiber surface was analyzed. The average content of molecular sieves on the fibers in the ten samples was 25 wt %, the standard deviation of the samples is 9 wt %, and the coefficient of variation is 36%, which indicates that the Y-type molecular sieve is unevenly distributed on the fiber surface.

Comparative Example 8

Refer to Chinese patent CN104888267A for experimental steps.

(1) A molecular sieve precursor solution was prepared, and a starting material was composed of $10Na_2O:Al_2O_3:9SiO_2:200H_2O$ in a molar ratio to synthesize a molecular sieve precursor solution.

(2) The molecular sieve precursor solution was heat-treated at 100° C. for 24 h to obtain a Y-type molecular sieve.

(3) Prepare polyurethane urea stock solution.

(4) The Y-type molecular sieve is ground in a dimethylacetamide solvent to obtain a Y-type molecular sieve solution.

(5) The polyurethane urea stock solution and the Y-type molecular sieve solution are simultaneously placed in a reaction container, and spandex fibers are prepared through a dry spinning process, and finally woven into a Y-type molecular sieve/spandex fiber hemostatic complex (blend spinning).

The difference between this Comparative Example and Example 1 is that the Y-type molecular sieve is blended and spun into the fiber, and there is no growth-matched coupling, and the molecular sieve and the fiber are simply physically mixed. In addition, the effective specific surface area of the molecular sieve becomes 126 $m^2g^{-1}$, the degree of calcium ion exchange becomes 45.9%, the degree of magnesium ion exchange becomes 27%, and the degree of strontium ion exchange becomes 12%. The blend spinning method is used to prepare hemostatic complex, which greatly reduces the effective contact area between the effective molecular sieve and the reaction system, and reduces the ion exchange and pore substance exchange capacity of the molecular sieve.

The difference between this Comparative Example and Example 1 is that the Y-type molecular sieve is blended and spun into the fiber. After detection by a scanning electron microscope, molecular sieve and fiber were simply physically mixed, and there was no growth-matched coupling. After testing, this method makes the effective specific surface area of the molecular sieve become 126 $m^2g^{-1}$, the degree of calcium ion exchange become 45.9%, the degree of magnesium ion exchange become 27%, and the degree of strontium ion exchange become 12%. The blend spinning method is used to prepare hemostatic complex, which greatly reduces the effective contact area between the effective molecular sieve and the reaction system, and reduces the ion exchange and pore substance exchange capacity of the molecular sieve.

Comparative Example 9

(i) A molecular sieve precursor solution was prepared, and a starting material was composed of $10Na_2O:Al_2O_3:9SiO_2:200H_2O$ in a molar ratio to synthesize a molecular sieve precursor solution. The molecular sieve precursor solution is mixed with cotton fiber, and the mass ratio of the cotton fiber and the molecular sieve precursor solution is 1:0.3.

(ii) The cotton fiber and the homogeneously-mixed molecular sieve precursor solution were heat-treated at 100° C. for 24 h to obtain a Y-type molecular sieve/cotton fiber complex. The content of Y-type molecular sieve was 90 wt %.

The difference between this Comparative Example and Example 1 is that the content of the Y-type molecular sieves is different. The content of the Y-type molecular sieves of this Comparative Example is greater than 80 wt %. After detection by a scanning electron microscope, the molecular sieves are clumped and wrapped on the fiber surface. The molecular sieves are not independently dispersed on the fiber surface, resulting in fiber stiffening. After testing, the agglomeration of molecular sieves makes the effective specific surface area of the molecular sieve become 346 $m^2g^{-1}$, the degree of calcium ion exchange become 53%, the degree of magnesium ion exchange become 52%, and the degree of strontium ion exchange become 42%. Both the effective specific surface area and ion exchange capacity are significantly reduced.

Example 2

The preparation method of the chabazite/cotton fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with cotton fiber, and the mass ratio of the cotton fiber and the molecular sieve precursor solution is 1:0.5.

(ii) The cotton fiber and the homogeneously-mixed molecular sieve precursor solution were heat-treated at 80° C. for 36 h to obtain a chabazite/cotton fiber hemostatic compound.

Ten samples of the prepared chabazite/cotton fiber hemostatic compound were randomly taken at different locations, and the content of the chabazite on the fiber surface was analyzed. The average content of molecular sieves on the fibers in the ten samples was 25 wt %, the standard deviation of the samples is 2.5 wt %, and the coefficient of variation is 10%, which indicates that the chabazite is uniformly distributed on the fiber surface.

Example 3

The preparation method of the X-type molecular sieve/silk fiber hemostatic compound of the present disclosure includes the following steps:

(i) A molecular sieve precursor solution was prepared, and a starting material was composed of $5.5Na_2O:1.65K_2O:Al_2O_3:2.2SiO_2:122H_2O$ in a molar ratio to synthesize a molecular sieve precursor solution. The molecular sieve precursor solution was mixed with silk fiber, and the mass ratio of the silk fiber and the molecular sieve precursor solution is 1:10.

(ii) The silk fiber and the homogeneously-mixed molecular sieve precursor solution were heat-treated at 100° C. for 12 h to obtain a X-type molecular sieve/silk fiber hemostatic compound.

Eight samples of the prepared X-type molecular sieve/silk fiber hemostatic compound were randomly taken at different locations, and the content of the X-type molecular sieve on the fiber surface was analyzed. The average content of molecular sieves on the fibers in the eight samples was 15 wt %, the standard deviation of the samples is 1.5 wt %, and the coefficient of variation is 10%, which indicates that the X-type molecular sieve is uniformly distributed on the fiber surface.

Example 4

The preparation method of the A-type molecular sieve/polyester fiber hemostatic compound of the present disclosure includes the following steps:

(i) A molecular sieve precursor solution was prepared, and a starting material was composed of $3Na_2O:Al_2O_3:2SiO_2:120H_2O$ in a molar ratio to synthesize a molecular sieve precursor solution. The molecular sieve precursor solution was mixed with polyester fiber, and the mass ratio of the polyester fiber and the molecular sieve precursor solution is 1:50.

(ii) The polyester fiber and the homogeneously-mixed molecular sieve precursor solution were heat-treated at 100° C. for 4 h to obtain a A-type molecular sieve/polyester fiber hemostatic compound.

Ten samples of the prepared A-type molecular sieve/polyester fiber hemostatic compound were randomly taken at different locations, and the content of the A-type molecular sieve on the fiber surface was analyzed. The average content of molecular sieves on the fibers in the ten samples was 50 wt %, the standard deviation of the samples is 7.5 wt %, and the coefficient of variation is 15%, which indicates that the A-type molecular sieve is uniformly distributed on the fiber surface.

Example 5

The preparation method of the ZSM-5 molecular sieve/polypropylene fiber hemostatic compound of the present disclosure includes the following steps:

(i) A molecular sieve precursor solution was prepared, and a starting material was composed of $3.5Na_2O:Al_2O_3:28SiO_2:900H_2O$ in a molar ratio to synthesize a molecular sieve precursor solution. The molecular sieve precursor solution was mixed with polypropylene fiber, and the mass ratio of the polypropylene fiber and the molecular sieve precursor solution is 1:200.

(ii) The polypropylene fiber and the homogeneously-mixed molecular sieve precursor solution were heat-treated at 180° C. for 42 h to obtain a ZSM-5 molecular sieve/polypropylene fiber hemostatic compound.

Ten samples of the prepared ZSM-5 molecular sieve/polypropylene fiber hemostatic compound were randomly taken at different locations, and the content of the ZSM-5 molecular sieve on the fiber surface was analyzed. The average content of molecular sieves on the fibers in the ten samples was 30 wt %, the standard deviation of the samples is 1.5 wt %, and the coefficient of variation is 5%, which indicates that the ZSM-5 molecular sieve is uniformly distributed on the fiber surface.

Example 6

The preparation method of the β-molecular sieve/rayon fiber hemostatic compound of the present disclosure includes the following steps:

(i) A molecular sieve precursor solution was prepared, and a starting material was composed of $2Na_2O:1.1K_2O\ Al_2O_3:50SiO_2:750H_2O:3HCl$ in a molar ratio to synthesize a molecular sieve precursor solution. The molecular sieve precursor solution was mixed with rayon fiber, and the mass ratio of the rayon fiber and the molecular sieve precursor solution is 1:100.

(ii) The rayon fiber and the homogeneously-mixed molecular sieve precursor solution were heat-treated at 135° C. for 25 h to obtain a β-molecular sieve/rayon fiber hemostatic compound.

Eight samples of the prepared β-molecular sieve/rayon fiber hemostatic compound were randomly taken at different locations, and the content of the β-molecular sieve on the fiber surface was analyzed. The average content of molecular sieves on the fibers in the eight samples was 25 wt %, the standard deviation of the samples is 2 wt %, and the coefficient of variation is 8%, which indicates that the β-molecular sieve is uniformly distributed on the fiber surface.

Example 7

The preparation method of the mordenite/acetate fiber hemostatic compound of the present disclosure includes the following steps:

(i) A molecular sieve precursor solution was prepared, and a starting material was composed of $5.5Na_2O:Al_2O_3:30SiO_2:810H_2O$ in a molar ratio to synthesize a molecular sieve precursor solution. The molecular sieve precursor solution was mixed with acetate fiber, and the mass ratio of the acetate fiber and the molecular sieve precursor solution is 1:300.

(ii) The acetate fiber and the homogeneously-mixed molecular sieve precursor solution were heat-treated at 170° C. for 24 h to obtain a mordenite/acetate fiber hemostatic compound.

Ten samples of the prepared mordenite/acetate fiber hemostatic compound were randomly taken at different locations, and the content of the mordenite on the fiber surface was analyzed. The average content of molecular sieves on the fibers in the ten samples was 35 wt %, the standard deviation of the samples is 5.25 wt %, and the coefficient of variation is 15%, which indicates that the mordenite is uniformly distributed on the fiber surface.

Example 8

The preparation method of the L-type molecular sieve/carboxymethyl cellulose hemostatic compound of the present disclosure includes the following steps:

(i) A molecular sieve precursor solution was prepared, and a starting material was composed of $2.5K_2O:Al_2O_3:12SiO_2:155H_2O$ in a molar ratio to synthesize a molecular sieve precursor solution. The molecular sieve precursor solution was mixed with carboxymethyl cellulose, and the mass ratio of the carboxymethyl cellulose and the molecular sieve precursor solution is 1:1.

(ii) The carboxymethyl cellulose and the homogeneously-mixed molecular sieve precursor solution were heat-treated at 220° C. for 50 h to obtain a L-type molecular sieve/carboxymethyl cellulose hemostatic compound.

Ten samples of the prepared L-type molecular sieve/carboxymethyl cellulose hemostatic compound were randomly taken at different locations, and the content of the L-type molecular sieve on the fiber surface was analyzed. The average content of molecular sieves on the fibers in the ten samples was 10 wt %, the standard deviation of the samples is 0.2 wt %, and the coefficient of variation is 2%, which indicates that the L-type molecular sieve is uniformly distributed on the fiber surface.

Example 9

The preparation method of the P-type molecular sieve/bamboo fiber hemostatic compound of the present disclosure includes the following steps:

(i) A molecular sieve precursor solution was prepared, and a starting material was composed of $10Na_2O:Al_2O_3:9SiO_2:400H_2O$ in a molar ratio to synthesize a molecular sieve precursor solution. The molecular sieve precursor solution was mixed with bamboo fiber, and the mass ratio of the bamboo fiber and the molecular sieve precursor solution is 1:2.

(ii) The bamboo fiber and the homogeneously-mixed molecular sieve precursor solution were heat-treated at 150° C. for 96 h to obtain a P-type molecular sieve/bamboo fiber hemostatic compound.

Twenty samples of the prepared P-type molecular sieve/bamboo fiber hemostatic compound were randomly taken at different locations, and the content of the P-type molecular sieve on the fiber surface was analyzed. The average content of molecular sieves on the fibers in the twenty samples was 80 wt %, the standard deviation of the samples is 4 wt %, and the coefficient of variation is 5%, which indicates that the P-type molecular sieve is uniformly distributed on the fiber surface.

Example 10

The preparation method of the merlinoite/linen fiber hemostatic compound of the present disclosure includes the following steps:

(i) A molecular sieve precursor solution was prepared, and a starting material was composed of $10Na_2O:Al_2O_3:9SiO_2:320H_2O$ in a molar ratio to synthesize a molecular sieve precursor solution. The molecular sieve precursor solution was mixed with linen fiber, and the mass ratio of the linen fiber and the molecular sieve precursor solution is 1:1000.

(ii) The linen fiber and the homogeneously-mixed molecular sieve precursor solution were heat-treated at 120° C. for 24 h to obtain a merlinoite/linen fiber hemostatic compound.

Fifteen samples of the prepared merlinoite/linen fiber hemostatic compound were randomly taken at different locations, and the content of the merlinoite on the fiber surface was analyzed. The average content of molecular sieves on the fibers in the fifteen samples was 30 wt %, the standard deviation of the samples is 0.3 wt %, and the coefficient of variation is 1%, which indicates that the merlinoite is uniformly distributed on the fiber surface.

Example 11

The preparation method of the X-type molecular sieve/wool hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with wool, and the mass ratio of the wool and the molecular sieve precursor solution is 1:20.

(ii) The wool and the homogeneously-mixed molecular sieve precursor solution were heat-treated at 60° C. for 16 h to obtain a X-type molecular sieve/wool hemostatic compound.

Fifteen samples of the prepared X-type molecular sieve/wool hemostatic compound were randomly taken at different locations, and the content of the X-type molecular sieve on the fiber surface was analyzed. The average content of molecular sieves on the fibers in the fifteen samples was 27 wt %, the standard deviation of the samples is 2.1 wt %, and the coefficient of variation is 7.8%, which indicates that the X-type molecular sieve is uniformly distributed on the fiber surface.

Example 12

The preparation method of the X-type molecular sieve/wood fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with wood fiber, and the mass ratio of the wood fiber and the molecular sieve precursor solution is 1:5. The content of X-type molecular sieve was 42 wt %.

(ii) The wood fiber and the homogeneously-mixed molecular sieve precursor solution were heat-treated at 90° C. for 24 h to obtain a X-type molecular sieve/wood fiber hemostatic compound.

Fifteen samples of the prepared X-type molecular sieve/wood fiber hemostatic compound were randomly taken at different locations, and the content of the X-type molecular sieve on the fiber surface was analyzed. The average content of molecular sieves on the fibers in the fifteen samples was 42 wt %, the standard deviation of the samples is 2.1 wt %, and the coefficient of variation is 5%, which indicates that the X-type molecular sieve is uniformly distributed on the fiber surface.

Example 13

The preparation method of the X-type molecular sieve/lactide polymer fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with lactide polymer fiber, and the mass ratio of the lactide polymer fiber and the molecular sieve precursor solution is 1:50.

(ii) The lactide polymer fiber and the homogeneously-mixed molecular sieve precursor solution were heat-treated at 90° C. for 30 h to obtain a X-type molecular sieve/lactide polymer fiber hemostatic compound. The content of X-type molecular sieve was 26 wt %.

Fifteen samples of the prepared X-type molecular sieve/lactide polymer fiber hemostatic compound were randomly taken at different locations, and the content of the X-type molecular sieve on the fiber surface was analyzed. The average content of molecular sieves on the fibers in the fifteen samples was 26 wt %, the standard deviation of the samples is 1.1 wt %, and the coefficient of variation is 4.2%, which indicates that the X-type molecular sieve is uniformly distributed on the fiber surface.

Example 14

The preparation method of the X-type molecular sieve/glycolide polymer fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with glycolide polymer fiber, and the mass ratio of the glycolide polymer fiber and the molecular sieve precursor solution is 1:200.

(ii) The glycolide polymer fiber and the homogeneously-mixed molecular sieve precursor solution were heat-treated at 120° C. for 24 h to obtain a X-type molecular sieve/glycolide polymer fiber hemostatic compound. The content of X-type molecular sieve was 37 wt %.

Fifteen samples of the prepared X-type molecular sieve/glycolide polymer fiber hemostatic compound were randomly taken at different locations, and the content of the X-type molecular sieve on the fiber surface was analyzed. The average content of molecular sieves on the fibers in the fifteen samples was 37 wt %, the standard deviation of the samples is 0.2 wt %, and the coefficient of variation is 0.5%, which indicates that the X-type molecular sieve is uniformly distributed on the fiber surface.

Example 15

The preparation method of the X-type molecular sieve/polylactide-glycolide polymer fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with polylactide-glycolide polymer fiber, and the mass ratio of the polylactide-glycolide polymer fiber and the molecular sieve precursor solution is 1:20.

(ii) The polylactide-glycolide polymer fiber and the homogeneously-mixed molecular sieve precursor solution were heat-treated at 90° C. for 24 h to obtain a X-type molecular sieve/polylactide-glycolide polymer fiber hemostatic compound. The content of X-type molecular sieve was 20 wt %.

Fifteen samples of the prepared X-type molecular sieve/polylactide-glycolide polymer fiber hemostatic compound were randomly taken at different locations, and the content of the X-type molecular sieve on the fiber surface was analyzed. The average content of molecular sieves on the fibers in the fifteen samples was 20 wt %, the standard deviation of the samples is 0.04 wt %, and the coefficient of variation is 0.2%, which indicates that the X-type molecular sieve is uniformly distributed on the fiber surface.

Example 16

The preparation method of the X-type molecular sieve/polyamide fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with polyamide fiber, and the mass ratio of the polyamide fiber and the molecular sieve precursor solution is 1:0.8.

(ii) The polyamide fiber and the homogeneously-mixed molecular sieve precursor solution were heat-treated at 90° C. for 24 h to obtain a X-type molecular sieve/polyamide fiber hemostatic compound. The content of X-type molecular sieve was 50 wt %.

Fifteen samples of the prepared X-type molecular sieve/polyamide fiber hemostatic compound were randomly taken at different locations, and the content of the X-type molecular sieve on the fiber surface was analyzed. The average content of molecular sieves on the fibers in the fifteen samples was 50 wt %, the standard deviation of the samples is 2 wt %, and the coefficient of variation is 4%, which indicates that the X-type molecular sieve is uniformly distributed on the fiber surface.

Example 17

The preparation method of the X-type molecular sieve/rayon-polyester fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with rayon-polyester fiber, and the mass ratio of the rayon-polyester fiber and the molecular sieve precursor solution is 1:50.

(ii) The rayon-polyester fiber and the homogeneously-mixed molecular sieve precursor solution were heat-treated at 110° C. for 28 h to obtain a X-type molecular sieve/rayon-polyester fiber hemostatic compound. The content of X-type molecular sieve was 5 wt %.

Eight samples of the prepared X-type molecular sieve/rayon-polyester fiber hemostatic compound were randomly taken at different locations, and the content of the X-type molecular sieve on the fiber surface was analyzed. The average content of molecular sieves on the fibers in the eight samples was 5 wt %, the standard deviation of the samples is 0.05 wt %, and the coefficient of variation is 1%, which indicates that the X-type molecular sieve is uniformly distributed on the fiber surface.

Example 18

The preparation method of the X-type molecular sieve/chitin fiber hemostatic compound of the present disclosure includes the following steps:

(i) A molecular sieve precursor solution was prepared, and a starting material was composed of $10Na_2O:Al_2O_3:9SiO_2:300H_2O$ in a molar ratio to synthesize a molecular sieve precursor solution. The molecular sieve precursor solution was mixed with chitin fiber, and the mass ratio of the chitin fiber and the molecular sieve precursor solution is 1:1.5.

(ii) The chitin fiber and the homogeneously-mixed molecular sieve precursor solution were heat-treated at 90° C. for 24 h to obtain a X-type molecular sieve/chitin fiber hemostatic compound. The content of X-type molecular sieve was 20 wt %.

Fifteen samples of the prepared X-type molecular sieve/chitin fiber hemostatic compound were randomly taken at different locations, and the content of the X-type molecular sieve on the fiber surface was analyzed. The average content of molecular sieves on the fibers in the fifteen samples was 20 wt %, the standard deviation of the samples is 2.5 wt %, and the coefficient of variation is 12.5%, which indicates that the X-type molecular sieve is uniformly distributed on the fiber surface.

Example 19

The preparation method of the $AlPO_4$-5 molecular sieve/polyethylene fiber hemostatic compound of the present disclosure includes the following steps:

(i) A molecular sieve precursor solution was prepared, and a starting material was composed of $Al_2O_3:1.3P_2O_5:1.3HF:425H_2O:6C_3H_7OH$ in a molar ratio to synthesize a molecular sieve precursor solution. The molecular sieve precursor solution was mixed with polyethylene fiber, and the mass ratio of the polyethylene fiber and the molecular sieve precursor solution is 1:20.

(ii) The polyethylene fiber and the homogeneously-mixed molecular sieve precursor solution were heat-treated at 180° C. for 6 h to obtain the $AlPO_4$-5 molecular sieve/polyethylene fiber hemostatic compound. The content of $AlPO_4$-5 molecular sieve was 18 wt %.

Fifteen samples of the prepared $AlPO_4$-5 molecular sieve/polyethylene fiber hemostatic compound were randomly taken at different locations, and the content of the $AlPO_4$-5 molecular sieve on the fiber surface was analyzed. The average content of molecular sieves on the fibers in the fifteen samples was 18 wt %, the standard deviation of the samples is 2.5 wt %, and the coefficient of variation is 13.9%, which indicates that the $AlPO_4$-5 molecular sieve is uniformly distributed on the fiber surface.

Example 20

The preparation method of the $AlPO_4$-11 molecular sieve/polyvinyl chloride fiber hemostatic compound of the present disclosure includes the following steps:

(i) A molecular sieve precursor solution was prepared, and a starting material was composed of $Al_2O_3:1.25P_2O_5:1.8HF:156H_2O$ in a molar ratio to synthesize a molecular sieve precursor solution. The molecular sieve precursor solution was mixed with polyvinyl chloride fiber, and the mass ratio of the polyvinyl chloride fiber and the molecular sieve precursor solution is 1:0.5.

(ii) The polyvinyl chloride fiber and the homogeneously-mixed molecular sieve precursor solution were heat-treated at 145° C. for 18 h to obtain the $AlPO_4$-11 molecular sieve/polyvinyl chloride fiber hemostatic compound. The content of $AlPO_4$-11 molecular sieve was 28 wt %.

Fifteen samples of the prepared $AlPO_4$-11 molecular sieve/polyvinyl chloride fiber hemostatic compound were randomly taken at different locations, and the content of the $AlPO_4$-11 molecular sieve on the fiber surface was analyzed. The average content of molecular sieves on the fibers in the fifteen samples was 28 wt %, the standard deviation of the samples is 2 wt %, and the coefficient of variation is 7.1%, which indicates that the $AlPO_4$-11 molecular sieve is uniformly distributed on the fiber surface.

Example 21

The preparation method of the SAPO-31 molecular sieve/polyacrylonitrile fiber hemostatic compound of the present disclosure includes the following steps:

(i) A molecular sieve precursor solution was prepared, and a starting material was composed of $Al_2O_3:P_2O_5:0.5SiO_2:60H_2O$ in a molar ratio to synthesize a molecular sieve precursor solution. The molecular sieve precursor solution was mixed with polyacrylonitrile fiber, and the mass ratio of the polyacrylonitrile fiber and the molecular sieve precursor solution is 1:1000.

(ii) The polyacrylonitrile fiber and the homogeneously-mixed molecular sieve precursor solution were heat-treated at 175° C. for 14.5 h to obtain a SAPO-31 molecular sieve/polyacrylonitrile fiber hemostatic compound. The content of SAPO-31 molecular sieve was 34 wt %.

Fifteen samples of the prepared SAPO-31 molecular sieve/polyacrylonitrile fiber hemostatic compound were randomly taken at different locations, and the content of the SAPO-31 molecular sieve on the fiber surface was analyzed. The average content of molecular sieves on the fibers in the fifteen samples was 34 wt %, the standard deviation of the samples is 5 wt %, and the coefficient of variation is 14.7%, which indicates that the SAPO-31 molecular sieve is uniformly distributed on the fiber surface.

Example 22

The preparation method of the SAPO-34 molecular sieve/viscose fiber hemostatic compound of the present disclosure includes the following steps:

(i) A molecular sieve precursor solution was prepared, and a starting material was composed of $Al_2O_3:1.06P_2O_5:1.08SiO_2:2.09$ morpholine$:60H_2O$ in a molar ratio to synthesize a molecular sieve precursor solution. The molecular sieve precursor solution was mixed with viscose fiber, and the mass ratio of the viscose fiber and the molecular sieve precursor solution is 1:20.

(ii) The viscose fiber and the homogeneously-mixed molecular sieve precursor solution were heat-treated at 175° C. for 14.5 h to obtain a SAPO-34 molecular sieve/viscose fiber hemostatic compound. The content of SAPO-34 molecular sieve was 1 wt %.

Fifteen samples of the prepared SAPO-34 molecular sieve/viscose fiber hemostatic compound were randomly taken at different locations, and the content of the SAPO-34 molecular sieve on the fiber surface was analyzed. The average content of molecular sieves on the fibers in the fifteen samples was 1 wt %, the standard deviation of the samples is 0.01 wt %, and the coefficient of variation is 1%, which indicates that the SAPO-34 molecular sieve is uniformly distributed on the fiber surface.

Example 23

The preparation method of the SAPO-11 molecular sieve/chitin fiber hemostatic compound of the present disclosure includes the following steps:

(i) A molecular sieve precursor solution was prepared, and a starting material was composed of $Al_2O_3:P_2O_5:0.5SiO_2:60H_2O$ in a molar ratio to synthesize a molecular sieve precursor solution. The molecular sieve precursor solution was mixed with chitin fiber, and the mass ratio of the chitin fiber and the molecular sieve precursor solution is 1:1.5.

(ii) The chitin fiber and the homogeneously-mixed molecular sieve precursor solution were heat-treated at 175° C. for 48 h to obtain a SAPO-11 molecular sieve/chitin fiber hemostatic compound. The content of SAPO-11 molecular sieve was 35 wt %.

Fifteen samples of the prepared SAPO-11 molecular sieve/chitin fiber hemostatic compound were randomly taken at different locations, and the content of the SAPO-11 molecular sieve on the fiber surface was analyzed. The average content of molecular sieves on the fibers in the fifteen samples was 35 wt %, the standard deviation of the samples is 1.5 wt %, and the coefficient of variation is 5%, which indicates that the SAPO-11 molecular sieve is uniformly distributed on the fiber surface.

Example 24

The preparation method of the BAC-1 molecular sieve/chitin fiber hemostatic compound of the present disclosure includes the following steps:

(i) A molecular sieve precursor solution was prepared, and a starting material was composed of $1.5B_2O_3:2.25Al_2O_3:2.5CaO:200H_2O$ in a molar ratio to synthesize a molecular sieve precursor solution. The molecular sieve precursor solution was mixed with chitin fiber, and the mass ratio of the chitin fiber and the molecular sieve precursor solution is 1:100.

(ii) The chitin fiber and the homogeneously-mixed molecular sieve precursor solution were heat-treated at 200° C. for 72 h to obtain a BAC-1 molecular sieve/chitin fiber hemostatic compound. The content of BAC-1 molecular sieve was 0.5 wt %.

Fifteen samples of the prepared BAC-1 molecular sieve/chitin fiber hemostatic compound were randomly taken at different locations, and the content of the BAC-1 molecular sieve on the fiber surface was analyzed. The average content of molecular sieves on the fibers in the fifteen samples was 0.5 wt %, the standard deviation of the samples is 0.04 wt %, and the coefficient of variation is 8%, which indicates that the BAC-1 molecular sieve is uniformly distributed on the fiber surface.

Example 25

The preparation method of the BAC-3 molecular sieve/chitin fiber hemostatic compound of the present disclosure includes the following steps:

(i) A molecular sieve precursor solution was prepared, and a starting material was composed of $3B_2O_3:Al_2O_3:0.7Na_2O:100H_2O$ in a molar ratio to synthesize a molecular sieve precursor solution. The molecular sieve precursor solution was mixed with chitin fiber, and the mass ratio of the chitin fiber and the molecular sieve precursor solution is 1:2.

(ii) The chitin fiber and the homogeneously-mixed molecular sieve precursor solution were heat-treated at 200° C. for 240 h to obtain a BAC-3 molecular sieve/chitin fiber hemostatic compound. The content of BAC-3 molecular sieve was 27 wt %.

Fifteen samples of the prepared BAC-3 molecular sieve/chitin fiber hemostatic compound were randomly taken at different locations, and the content of the BAC-3 molecular sieve on the fiber surface was analyzed. The average content of molecular sieves on the fibers in the fifteen samples was 27 wt %, the standard deviation of the samples is 0.08 wt %, and the coefficient of variation is 0.3%, which indicates that the BAC-3 molecular sieve is uniformly distributed on the fiber surface.

Example 26

The preparation method of the BAC-10 molecular sieve/chitin fiber hemostatic compound of the present disclosure includes the following steps:

(i) A molecular sieve precursor solution was prepared, and a starting material was composed of $2.5B_2O_3:2Al_2O_3:CaO:200H_2O$ in a molar ratio to synthesize a molecular sieve precursor solution. The molecular sieve precursor solution was mixed with chitin fiber, and the mass ratio of the chitin fiber and the molecular sieve precursor solution is 1:20.

(ii) The chitin fiber and the homogeneously-mixed molecular sieve precursor solution were heat-treated at 160° C. for 72 h to obtain a BAC-10 molecular sieve/chitin fiber hemostatic compound. The content of BAC-10 molecular sieve was 21 wt %.

Fifteen samples of the prepared BAC-10 molecular sieve/chitin fiber hemostatic compound were randomly taken at different locations, and the content of the BAC-10 molecular sieve on the fiber surface was analyzed. The average content of molecular sieves on the fibers in the fifteen samples was 21 wt %, the standard deviation of the samples is 0.9 wt %, and the coefficient of variation is 4.2%, which indicates that the BAC-10 molecular sieve is uniformly distributed on the fiber surface.

Comparative Examples 10 and 11

Commercially available granular molecular sieve materials (Quikclot) and Combat Gauze from Z-Medica Co., Ltd., were taken as Comparative Examples 10 and 11, respectively. The hemostatic function of the materials was evaluated using a rabbit femoral artery lethal model.

Figure 17A:
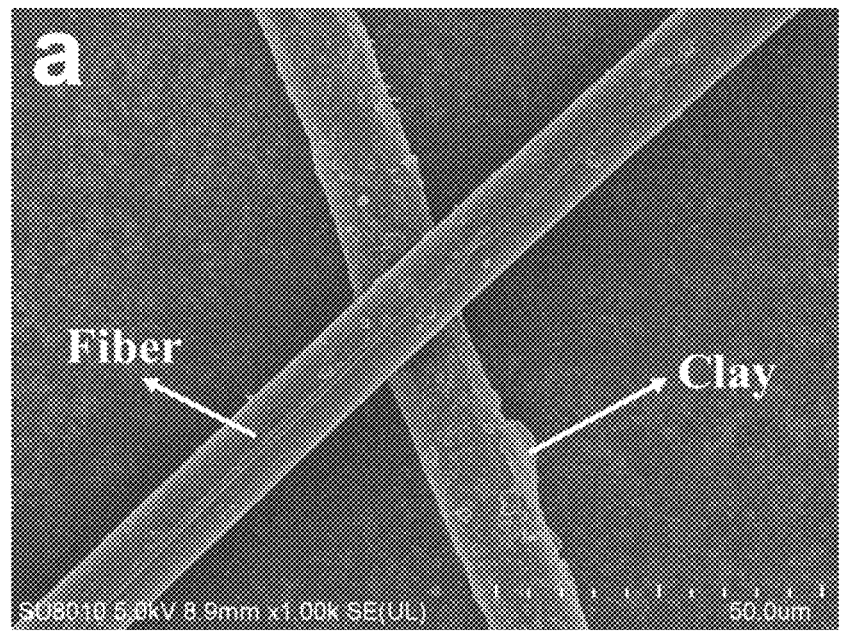
FIG. 17A is a scanning electron microscope image of Combat Gauze commercialized by Z-Medica Co., Ltd. in Comparative Example 11 (Bar=50 μm).
Figure 17B:
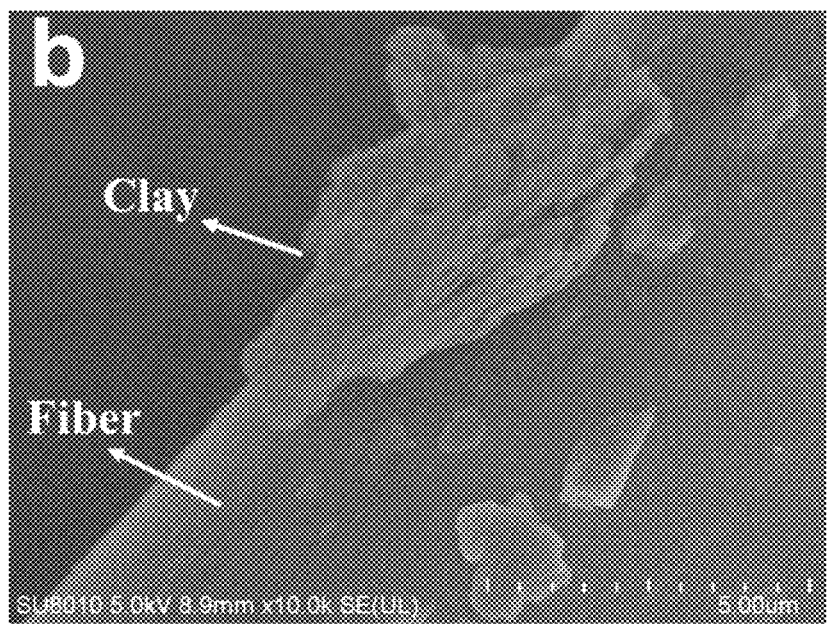
FIG. 17B is a scanning electron microscope image of Combat Gauze commercialized by Z-Medica Co., Ltd. in Comparative Example 11 (Bar=5 μm)
Figure 18:
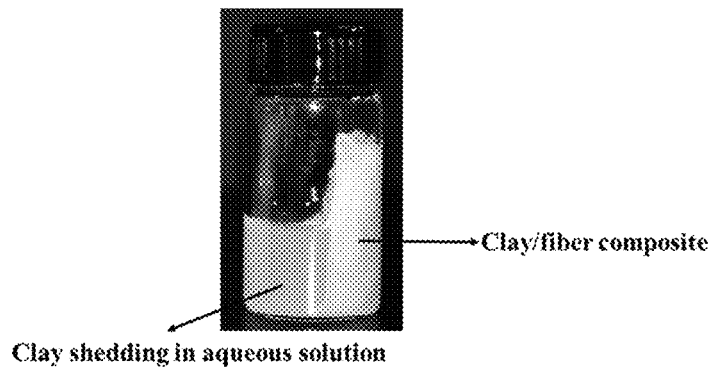
FIG. 18 is a picture of a clay/fiber composite in an aqueous solution in the prior art.
Figure 19:
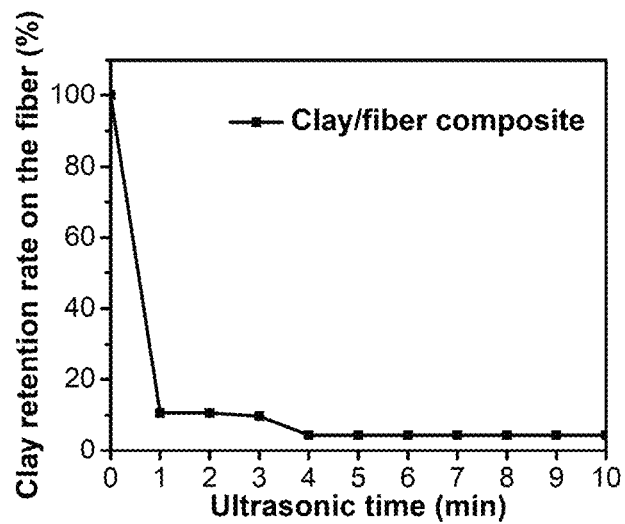
FIG. 19 is a graph of clay retention rate of clay/fiber composite of a prior art in an aqueous solution under ultrasonic condition for different times.

Among them, the commercial Combat Gauze is an inorganic hemostatic material (clay, kaolin) attached to the fiber surface. Observed from the scanning electron microscope, the inorganic hemostatic material is unevenly distributed on the fiber surface, as shown in FIGS. 17A-17B, and the material is not bonded to the fiber surface, and it is easy to fall off from the fiber surface. Clay retention rate on the gauze fiber is 10% or less under ultrasonic condition for 1 min; clay retention rate on the gauze fiber is 5% or less under ultrasonic condition for 5 min (FIG. 18); clay retention rate on the gauze fiber is 5% or less under ultrasonic condition for 20 min. This defective structural form limits the hemostatic properties of the hemostatic product and risks causing sequelae or other side effects.

The certain size of the molecular sieve in the hemostatic compound can promote the uniform distribution of the molecular sieve on the fiber surface. The size of the molecular sieve and the average particle diameters of the inner and outer surface nanoparticles in the synthetic hemostatic compound of Examples 1-26 are shown in Table 1, according to the observation of the scanning electron microscope. In order to evaluate the binding strength between the molecular sieve and the fiber, the synthetic hemostatic compounds of Examples 1-26 were ultrasonicated in deionized water for 20, 40, 60, and 80 minutes, respectively. After ultrasonic testing, the retention rates of the molecular sieve on the fibers are shown in Table 2. In order to show that the molecular sieve in the hemostatic compound of the present disclosure maintains a good structure and performance on the fiber, after testing, the effective specific surface area and ion exchange capacity of the molecular sieve of Example 1-26 are shown in Table 3. In order to illustrate the superior hemostatic properties of hemostatic compounds, a rabbit femoral artery lethal model was used to evaluate the hemostatic function of hemostatic materials of Examples 1-26 and Comparative Example. After observing and testing, statistical data of hemostatic performance are shown in Table 4.

TABLE 1

The particle size of molecular sieve of the molecular sieve/fiber hemostatic compound and the average particle size of the nanoparticles on the inner and outer surfaces

| Serial number | Material | Molecular sieve D90/μm | Molecular sieve D50/μm | Average particle size of the nanoparticles on the outer surfaces/nm | Average particle size of the nanoparticles on the inner surfaces/nm |
|---|---|---|---|---|---|
| Example 1 | Y-type molecular sieve/cotton fiber hemostatic compound | 25 | 5 | 148 | 61 |
| Example 2 | Chabazite/cotton fiber hemostatic compound | 4 | 2 | 200 | 31 |
| Example 3 | X-type molecular sieve/silk fiber hemostatic compound | 20 | 10 | 256 | 51 |
| Example 4 | A-type molecular sieve/polyester fiber hemostatic compound | 50 | 30 | 141 | 12 |
| Example 5 | ZSM-5 molecular sieve/polypropylene fiber hemostatic compound | 30 | 15 | 190 | 11 |
| Example 6 | β-molecular sieve/rayon fiber hemostatic compound | 6 | 4 | 110 | 33 |
| Example 7 | Mordenite/acetate fiber hemostatic compound | 7 | 3 | 109 | 23 |
| Example 8 | L-type molecular sieve/carboxymethyl cellulose hemostatic compound | 8 | 5.5 | 300 | 22 |
| Example 9 | P-type molecular sieve/bamboo fiber hemostatic compound | 10 | 8 | 240 | 60 |
| Example 10 | Merlinoite/linen fiber hemostatic compound | 5 | 1 | 200 | 12 |
| Example 11 | X-type molecular sieve/wool hemostatic compound | 10 | 5 | 240 | 4 |
| Example 12 | X-type molecular sieve/wood fiber hemostatic compound | 0.1 | 0.05 | 3 | 2 |
| Example 13 | X-type molecular sieve/lactide polymer fiber hemostatic compound | 0.01 | 0.005 | 3 | 2 |
| Example 14 | X-type molecular sieve/glycolide polymer fiber hemostatic compound | 0.5 | 0.25 | 10 | 4 |
| Example 15 | X-type molecular sieve/polylactide-glycolide polymer fiber hemostatic compound | 1 | 0.5 | 30 | 20 |
| Example 16 | X-type molecular sieve/polyamide fiber hemostatic compound | 5 | 2.5 | 30 | 20 |
| Example 17 | X-type molecular sieve/rayon-polyester fiber hemostatic compound | 20 | 13 | 195 | 68 |
| Example 18 | X-type molecular sieve/chitin fiber hemostatic compound | 20 | 10 | 150 | 100 |
| Example 19 | AlPO$_4$-5 molecular sieve/polyethylene fiber hemostatic compound | 7.5 | 5.5 | 500 | 22 |
| Example 20 | AlPO$_4$-11 molecular sieve/polyvinyl chloride fiber hemostatic compound | 5 | 4 | 200 | 2 |
| Example 21 | SAPO-31 molecular sieve/polyacrylonitrile fiber hemostatic compound | 3 | 3 | 109 | 25 |
| Example 22 | SAPO-34 molecular sieve/viscose fiber hemostatic compound | 5 | 4 | 110 | 33 |
| Example 23 | SAPO-11 molecular sieve/chitin fiber hemostatic compound | 8 | 5 | 211 | 10 |
| Example 24 | BAC-1 molecular sieve/chitin fiber hemostatic compound | 12 | 10 | 256 | 51 |
| Example 25 | BAC-3 molecular sieve/chitin fiber hemostatic compound | 15 | 8 | 500 | 32 |
| Example 26 | BAC-10 molecular sieve/chitin fiber hemostatic compound | 10 | 8 | 50 | 4 |

TABLE 2

The binding strength of molecular sieve and fiber of molecular sieve/fiber hemostatic compound

| Serial number | Material | Retention rate of molecular sieves on fibers under ultrasonic condition for 20 min | Retention rate of molecular sieves on fibers under ultrasonic condition for 40 min | Retention rate of molecular sieves on fibers under ultrasonic condition for 60 min | Retention rate of molecular sieves on fibers under ultrasonic condition for 80 min |
|---|---|---|---|---|---|
| Example 1 | Y-type molecular sieve/cotton fiber hemostatic compound | 100% | 100% | 100% | 100% |
| Example 2 | Chabazite/cotton fiber hemostatic compound | 100% | 100% | 100% | 100% |
| Example 3 | X-type molecular sieve/silk fiber hemostatic compound | 95% | 95% | 95% | 95% |
| Example 4 | A-type molecular sieve/polyester fiber hemostatic compound | 100% | 100% | 100% | 100% |
| Example 5 | ZSM-5 molecular sieve/polypropylene fiber hemostatic compound | 98% | 98% | 98% | 98% |
| Example 6 | β-molecular sieve/rayon fiber hemostatic compound | 100% | 100% | 100% | 100% |
| Example 7 | Mordenite/acetate fiber hemostatic compound | 91% | 91% | 91% | 91% |
| Example 8 | L-type molecular sieve/carboxymethyl cellulose hemostatic compound | 99% | 99% | 99% | 99% |
| Example 9 | P-type molecular sieve/bamboo fiber hemostatic compound | 100% | 100% | 100% | 100% |
| Example 10 | Merlinoite/linen fiber hemostatic compound | 100% | 100% | 100% | 100% |
| Example 11 | X-type molecular sieve/wool hemostatic compound | 90% | 90% | 90% | 90% |
| Example 12 | X-type molecular sieve/wood fiber hemostatic compound | 100% | 100% | 100% | 100% |
| Example 13 | X-type molecular sieve/lactide polymer fiber hemostatic compound | 100% | 100% | 100% | 100% |
| Example 14 | X-type molecular sieve/glycolide polymer fiber hemostatic compound | 100% | 100% | 100% | 100% |
| Example 15 | X-type molecular sieve/polylactide-glycolide polymer fiber hemostatic compound | 100% | 100% | 100% | 100% |
| Example 16 | X-type molecular sieve/polyamide fiber hemostatic compound | 94% | 94% | 94% | 94% |
| Example 17 | X-type molecular sieve/rayon-polyester fiber hemostatic compound | 96% | 96% | 96% | 96% |
| Example 18 | X-type molecular sieve/chitin fiber hemostatic compound | 91% | 91% | 91% | 91% |
| Example 19 | $AlPO_4$-5 molecular sieve/polyethylene fiber hemostatic compound | 100% | 100% | 100% | 100% |
| Example 20 | $AlPO_4$-11 molecular sieve/polyvinyl chloride fiber hemostatic compound | 100% | 100% | 100% | 100% |
| Example 21 | SAPO-31 molecular sieve/polyacrylonitrile fiber hemostatic compound | 90% | 90% | 90% | 90% |
| Example 22 | SAPO-34 molecular sieve/viscose fiber hemostatic compound | 100% | 100% | 100% | 100% |
| Example 23 | SAPO-11 molecular sieve/chitin fiber hemostatic compound | 100% | 100% | 100% | 100% |
| Example 24 | BAC-1 molecular sieve/chitin fiber hemostatic compound | 100% | 100% | 100% | 100% |
| Example 25 | BAC-3 molecular sieve/chitin fiber hemostatic compound | 100% | 100% | 100% | 100% |
| Example 26 | BAC-10 molecular sieve/chitin fiber hemostatic compound | 99% | 99% | 99% | 99% |

TABLE 3

Effective specific surface area and ion exchange capacity of molecular sieves with different hemostatic compound

| Serial number | Material | Effective specific surface area of molecular sieves/($m^2g^{-1}$) | Degree of calcium ion exchange | Degree of magnesium ion exchange | Degree of Strontium ion exchange |
| --- | --- | --- | --- | --- | --- |
| Example 1 | Y-type molecular sieve/cotton fiber hemostatic compound | 490 | 99.9% | 97% | 90% |
| Example 2 | Chabazite/cotton fiber hemostatic compound | 853 | 90.2% | 92% | 80% |
| Example 3 | X-type molecular sieve/silk fiber hemostatic compound | 741 | 91% | 81% | 80% |
| Example 4 | A-type molecular sieve/polyester fiber hemostatic compound | 502 | 85% | 77% | 70% |
| Example 5 | ZSM-5 molecular sieve/polypropylene fiber hemostatic compound | 426 | 80% | 77% | 70% |
| Example 6 | β-molecular sieve/rayon fiber hemostatic compound | 763 | 95% | 87% | 85% |
| Example 7 | Mordenite/acetate fiber hemostatic compound | 412 | 95% | 87% | 85% |
| Example 8 | L-type molecular sieve/carboxymethyl cellulose hemostatic compound | 858 | 85% | 81% | 80% |
| Example 9 | P-type molecular sieve/bamboo fiber hemostatic compound | 751 | 91% | 90% | 85% |
| Example 10 | Merlinoite/linen fiber hemostatic compound | 510 | 98.5% | 97% | 90% |
| Example 11 | X-type molecular sieve/wool hemostatic compound | 494 | 98% | 97% | 91% |
| Example 12 | X-type molecular sieve/wood fiber hemostatic compound | 492 | 99% | 97% | 93% |
| Example 13 | X-type molecular sieve/lactide polymer fiber hemostatic compound | 496 | 98.9% | 97% | 90% |
| Example 14 | X-type molecular sieve/glycolide polymer fiber hemostatic compound | 480 | 97% | 97% | 91% |
| Example 15 | X-type molecular sieve/polylactide-glycolide polymer fiber hemostatic compound | 499 | 99.7% | 95% | 87% |
| Example 16 | X-type molecular sieve/polyamide fiber hemostatic compound | 495 | 95% | 94% | 90% |
| Example 17 | X-type molecular sieve/rayon-polyester fiber hemostatic compound | 846 | 91.2% | 90% | 83% |
| Example 18 | X-type molecular sieve/chitin fiber hemostatic compound | 751 | 91% | 90% | 85% |
| Example 19 | AlPO$_4$-5 molecular sieve/polyethylene fiber hemostatic compound | 426 | — | — | — |
| Example 20 | AlPO$_4$-11 molecular sieve/polyvinyl chloride fiber hemostatic compound | 763 | — | — | — |
| Example 21 | SAPO-31 molecular sieve/polyacrylonitrile fiber hemostatic compound | 412 | — | — | — |
| Example 22 | SAPO-34 molecular sieve/viscose fiber hemostatic compound | 858 | — | — | — |
| Example 23 | SAPO-11 molecular sieve/chitin fiber hemostatic compound | 510 | — | — | — |
| Example 24 | BAC-1 molecular sieve/chitin fiber hemostatic compound | 494 | — | — | — |
| Example 25 | BAC-3 molecular sieve/chitin fiber hemostatic compound | 492 | — | — | — |
| Example 26 | BAC-10 molecular sieve/chitin fiber hemostatic compound | 496 | — | — | — |

TABLE 4

Hemostatic function of different hemostatic materials

| Serial number | Hemostatic material | Hemostatic time | Rising temperature of wound (° C.) | Blood loss (g) | Ease of use | Debridement effect | Wound condition | Survival rate |
|---|---|---|---|---|---|---|---|---|
| Example 1 | Y-type molecular sieve/cotton fiber hemostatic compound | 2 min | No | 4 ± 0.5 | Tailored for wound size and practical needs | Easy to remove, no other removal required | Dry and well healed | 100% |
| Example 2 | Chabazite/cotton fiber hemostatic compound | 1.8 min | No | 3 ± 0.5 | Tailored for wound size and practical needs | Easy to remove, no other removal required | Dry and well healed | 100% |
| Example 3 | X-type molecular sieve/silk fiber hemostatic compound | 1.8 min | No | 3 ± 0.4 | Tailored for wound size and practical needs | Easy to remove, no other removal required | Dry and well healed | 100% |
| Example 4 | A-type molecular sieve/polyester fiber hemostatic compound | 2 min | No | 3 ± 0.8 | Tailored for wound size and practical needs | Easy to remove, no other removal required | Dry and well healed | 100% |
| Example 5 | ZSM-5 molecular sieve/polypropylene fiber hemostatic compound | 2.5 min | No | 4 ± 0.8 | Tailored for wound size and practical needs | Easy to remove, no other removal required | Dry and well healed | 100% |
| Example 6 | β-molecular sieve/rayon fiber hemostatic compound | 2 min | No | 3 ± 0.8 | Tailored for wound size and practical needs | Easy to remove, no other removal required | Dry and well healed | 100% |
| Example 7 | Mordenite/acetate fiber hemostatic compound | 2.1 min | No | 3.5 ± 0.4 | Tailored for wound size and practical needs | Easy to remove, no other removal required | Dry and well healed | 100% |
| Example 8 | L-type molecular sieve/carboxymethyl cellulose hemostatic compound | 2.7 min | No | 4.2 ± 0.4 | Tailored for wound size and practical needs | Easy to remove, no other removal required | Dry and well healed | 100% |
| Example 9 | P-type molecular sieve/bamboo fiber hemostatic compound | 2.4 min | No | 4.3 ± 0.7 | Tailored for wound size and practical needs | Easy to remove, no other removal required | Dry and well healed | 100% |
| Example 10 | Merlinoite/linen fiber hemostatic compound | 2.4 min | No | 4.3 ± 0.7 | Tailored for wound size and practical needs | Easy to remove, no other removal required | Dry and well healed | 100% |
| Example 11 | X-type molecular sieve/wool hemostatic compound | 2 min | No | 4 ± 0.5 | Tailored for wound size and practical needs | Easy to remove, no other removal required | Dry and well healed | 100% |
| Example 12 | X-type molecular sieve/wood fiber hemostatic compound | 2.1 min | No | 4 ± 0.5 | Tailored for wound size and practical needs | Easy to remove, no other removal required | Dry and well healed | 100% |

TABLE 4-continued

Hemostatic function of different hemostatic materials

| Serial number | Hemostatic material | Hemostatic time | Rising temperature of wound (° C.) | Blood loss (g) | Ease of use | Debridement effect | Wound condition | Survival rate |
|---|---|---|---|---|---|---|---|---|
| Example 13 | X-type molecular sieve/lactide polymer fiber hemostatic compound | 2.4 min | No | 4.3 ± 0.3 | Tailored for wound size and practical needs | Easy to remove, no other removal required | Dry and well healed | 100% |
| Example 14 | X-type molecular sieve/glycolide polymer fiber hemostatic compound | 2.1 min | No | 3.5 ± 0.5 | Tailored for wound size and practical needs | Easy to remove, no other removal required | Dry and well healed | 100% |
| Example 15 | X-type molecular sieve/polylactide-glycolide polymer fiber hemostatic compound | 2.3 min | No | 3.8 ± 0.5 | Tailored for wound size and practical needs | Easy to remove, no other removal required | Dry and well healed | 100% |
| Example 16 | X-type molecular sieve/polyamide fiber hemostatic compound | 2.5 min | No | 4.2 ± 0.5 | Tailored for wound size and practical needs | Easy to remove, no other removal required | Dry and well healed | 100% |
| Example 17 | X-type molecular sieve/rayon-polyester fiber hemostatic compound | 2.4 min | No | 4.4 ± 0.5 | Tailored for wound size and practical needs | Easy to remove, no other removal required | Dry and well healed | 100% |
| Example 18 | X-type molecular sieve/chitin fiber hemostatic compound | 2 min | No | 3 ± 0.8 | Tailored for wound size and practical needs | Easy to remove, no other removal required | Dry and well healed | 100% |
| Example 19 | $AlPO_4$-5 molecular sieve/polyethylene fiber hemostatic compound | 2 min | No | 3 ± 0.8 | Tailored for wound size and practical needs | Easy to remove, no other removal required | Dry and well healed | 100% |
| Example 20 | $AlPO_4$-11 molecular sieve/polyvinyl chloride fiber hemostatic compound | 2.1 min | No | 3.5 ± 0.4 | Tailored for wound size and practical needs | Easy to remove, no other removal required | Dry and well healed | 100% |
| Example 21 | SAPO-31 molecular sieve/polyacrylonitrile fiber hemostatic compound | 2.1 min | No | 3.2 ± 0.4 | Tailored for wound size and practical needs | Easy to remove, no other removal required | Dry and well healed | 100% |
| Example 22 | SAPO-34 molecular sieve/viscose fiber hemostatic compound | 2.4 min | No | 4 ± 0.7 | Tailored for wound size and practical needs | Easy to remove, no other removal required | Dry and well healed | 100% |
| Example 23 | SAPO-11 molecular sieve/chitin fiber hemostatic compound | 2.5 min | No | 4.2 ± 0.5 | Tailored for wound size and practical needs | Easy to remove, no other removal required | Dry and well healed | 100% |
| Example 24 | BAC-1 molecular sieve/chitin fiber hemostatic compound | 2.4 min | No | 4.4 ± 0.5 | Tailored for wound size and practical needs | Easy to remove, no other removal required | Dry and well healed | 100% |

TABLE 4-continued

Hemostatic function of different hemostatic materials

| Serial number | Hemostatic material | Hemostatic time | Rising temperature of wound (° C.) | Blood loss (g) | Ease of use | Debridement effect | Wound condition | Survival rate |
| --- | --- | --- | --- | --- | --- | --- | --- | --- |
| Example 25 | BAC-3 molecular sieve/chitin fiber hemostatic compound | 2 min | No | 3 ± 0.8 | Tailored for wound size and practical needs | Easy to remove, no other removal required | Dry and well healed | 100% |
| Example 26 | BAC-10 molecular sieve/chitin fiber hemostatic compound | 2.4 min | No | 3.4 ± 0.1 | Tailored for wound size and practical needs | Easy to remove, no other removal required | Dry and well healed | 100% |
| Comparative Example 2 | Y-type molecular sieve/cotton fiber hemostatic complex (impregnation method) | 5.4 min | 2 ± 1 | 7.4 ± 0.1 | Tailored for wound size and practical needs | Part of the molecular sieves fall from the fiber and stick to the wound, making them difficult to remove | A large blood clot forms on the surface of the wound, which is gererally healed | 60% |
| Comparative Example 3 | Y-type molecular sieve/cotton fiber hemostatic complex (spray method) | 5.2 min | 3 ± 1 | 7.6 ± 0.1 | Tailored for wound size and practical needs | Part of the molecular sieves fall from the fiber and stick to the wound, making them difficult to remove | A large blood clot forms on the surface of the wound, which is gererally healed | 55% |
| Comparative Example 4 | Y-type molecular sieve/cotton fiber hemostatic complex (including adhesive 1) | 6.2 min | 7 ± 1 | 5.5 ± 0.2 | Tailored for wound size and practical needs | Part of the molecular sieves fall from the fiber and stick to the wound, making them difficult to remove | A large blood clot forms on the surface of the wound, which is gererally healed | 65% |
| Comparative Example 5 | Y-type molecular sieve/cotton fiber hemostatic complex (including adhesive 2) | 5.4 min | 4 ± 1 | 8.5 ± 0.2 | Tailored for wound size and practical needs | Part of the molecular sieves fall from the fiber and stick to the wound, making them difficult to remove | A large blood clot forms on the surface of the wound, which is gererally healed | 45% |
| Comparative Example 6 | Y-type molecular sieve/cotton fiber hemostatic complex (including adhesive 3) | 6 min | 2 ± 1 | 7.5 ± 0.1 | Tailored for wound size and practical needs | Part of the molecular sieves fall from the fiber and stick to the wound, making them difficult to remove | A large blood clot forms on the surface of the wound, which is gererally healed | 40% |
| Comparative Example 7 | Y-type molecular sieve/cotton fiber hemostatic complex (pretreatment of fiber) | 6.5 min | 2 ± 1 | 7.1 ± 0.1 | hard and brittle, and does not make good contact with the wound | Part of the molecular sieves fall from the fiber and stick to the wound, making them difficult to remove | A large blood clot forms on the surface of the wound, which is gererally healed | 45% |

TABLE 4-continued

Hemostatic function of different hemostatic materials

| Serial number | Hemostatic material | Hemostatic time | Rising temperature of wound (° C.) | Blood loss (g) | Ease of use | Debridement effect | Wound condition | Survival rate |
|---|---|---|---|---|---|---|---|---|
| Comparative Example 8 | Y-type molecular sieve/spandex fiber hemostatic complex (blend spinning) | 5.4 min | No | 9.1 ± 0.1 | Tailored for wound size and practical needs | Easy to remove, no other removal required | A large blood clot forms on the surface of the wound, which is gererally healed | 40% |
| Comparative Example 10 | Quikclot molecular sieve granule | 3 min | 10 ± 2 | 6.5 ± 0.9 | Difficult to adjust dosage | The granules need to be washed serveral time with physiological saline, and can plug in blood vessels | The wound with slight burns was washed by physiological saline, and it was easy to rebleed. | 50% |
| Comparative Example 11 | Combat Gauze (Clay/fiber hemostatic complex) | 7.5 min | No | 12.7 ± 0.8 | Tailored for wound size and practical needs | Part of the clay falls off the fibers. Due to the large amount of bleeding, a large area of blood clot is formed on the wound surface, which adheres to the wound surface and is easy to rebleed when cleared. | A large blood clot forms on the wound surface, making it difficult to observe the actual blood vessel healing | 40% |

The above results show that: Examples 1-26 list the molecular sieve/fiber hemostatic compounds with different molecular sieves and different fibers, and the inner surface of the molecular sieve of the molecular sieve/fiber hemostatic compounds of Examples 1-26 in contact with the fibers is a rough planar surface matched with the fiber surface. Ultrasound the molecular sieve/fiber hemostatic compounds in deionized water for ≥20 min, and use a thermogravimetric analyzer to analyze the content of molecular sieves on the fiber surface. The retention rate of molecular sieves is ≥90%, indicating that a growth-matched coupling is formed between the molecular sieve and the fiber. The molecular sieve is firmly bonded to the fiber. The adhesive content of the contact surface between the molecular sieve and the fiber is zero in Examples 1-26 of the present disclosure, and the degree of calcium ion exchange of the molecular sieve is ≥90%, the degree of magnesium ion exchange is ≥75%, and the degree of strontium ion exchange is ≥70%. It overcomes the defects of high synthetic cost, low effective surface area, and clogging of molecular sieve channels, which exists on the fibers through the adhesive. Although the molecular sieve/fiber hemostatic compound has a reduced amount of molecular sieve compared to the molecular sieve granules, the hemostatic effect of the molecular sieve/fiber hemostatic compound is better than the commercial molecular sieve granules (Quikclot), which further solves the problem of water absorption and heat release. The molecular sieve of the present disclosure is uniformly distributed on the fiber surface with a certain size, and a growth-matched coupling is formed between the molecular sieve and the fiber. The molecular sieve has a strong binding strength with the fiber. The molecular sieve has a high effective specific surface area and substance exchange capacity on the fiber surface. The hemostatic effect of hemostatic compounds is superior to that of composite materials with weak binding strength between molecular sieves and fiber or low effective specific surface area or low material exchange capacity in the prior art. The hemostatic compounds have a short hemostatic time, low blood loss, and high survival rate in the rabbit femoral artery lethal model, and the molecular sieve/fiber compounds are safe during hemostatic process. In addition, the hemostatic compounds also have the following advantages: (i) the wound surface after hemostasis is easy to clean up and convenient for post-processing by professionals; (ii) hemostatic compounds can be tailored for wound size and practical needs; (iii) the wound after hemostasis is dry and heals well after treated with the hemostatic compounds.

The above embodiments are only used to illustrate the present disclosure and are not used to limit the scope of the present disclosure. In addition, it should be understood that after reading the teaching of the present disclosure, those skilled in the art can make various changes or modifications to the present disclosure, and these equivalent forms also fall within the scope defined by the appended claims of the present application.

What is claimed is:

1. A hemostatic compound, comprising molecular sieves and a fiber,
wherein the molecular sieves are independently dispersed on a fiber surface of the fiber without agglomeration; when randomly taking n samples of the hemostatic compound at different locations and analyzing a content of the molecular sieves on the fiber surface, a coefficient of variation of the content of the molecular sieves in the n samples is ≤15%; wherein n is a positive integer greater than or equal to 8;
the molecular sieves directly contact the fiber surface;
a first surface of the molecular sieve contacted with the fiber is defined as an inner surface, and a second surface of the molecular sieve uncontacted with the fiber is defined as an outer surface;
wherein the inner surface is a rough and planer surface matched with the fiber surface;
the molecular sieve forms a growth-matched coupling with the fiber on the inner surface, and the growth-matched coupling refers to that a plurality of molecular sieve microparticles grow to match the fiber surface to form a tightly-coupled coupling interface that matches the fiber surface;
a first particle size D90 of the molecular sieve microparticles is 0.01 to 50 μm, a second particle size D50 of the molecular sieve microparticles is 0.005 to 30 μm; both the inner surface and the outer surface are composed of molecular sieve nanoparticles; the first particle size D90 refers to a particle size corresponding to a cumulative particle size distribution percentage of the molecular sieve microparticles on the surface of the hemostatic compound reaching 90%; the second particle size D50 refers to a particle size corresponding to a cumulative particle size distribution percentage of the molecular sieve microparticles on the surface of the hemostatic compound reaching 50% wherein the molecular sieve is selected from the group consisting of X-type zeolite molecular sieve, Y-type zeolite molecular sieve, A-type zeolite molecular sieve, ZSM-5 (Zeolite Socony Mobil-5) molecular sieve, chabazite, β-zeolite molecular sieve, mordenite, L-type zeolite molecular sieve, P-type zeolite molecular sieve, merlinoite, $AlPO_4$-5 (Aluminophosphate) molecular sieve, $AlPO_4$-11 molecular sieve, SAPO-31 (Silicoaluminophosphate) molecular sieve, SAPO-34 molecular sieve, SAPO-11 molecular sieve, BAC-1 (Boron-Aluminum OxO-Chloride) molecular sieve, BAC-3 molecular sieve, BAC-10 molecular sieve, and combination thereof, and wherein the fiber is selected from of the group consisting of silk fiber, chitin fiber, rayon fiber, acetate fiber, carboxymethyl cellulose, bamboo fiber, cotton fiber, linen fiber, wool, wood fiber, lactide polymer fiber, glycolide polymer fiber, polyester fiber, polyamide fiber, polypropylene fiber, polyethylene fiber, polyvinyl chloride fiber, polyacrylonitrile fiber, viscose fiber, and combination thereof.

2. The hemostatic compound of claim 1, wherein the inner surface is the planar surface matched with the fiber surface and the outer surface is a non-planar surface.

3. The hemostatic compound of claim 1, wherein each of the molecular sieves independently dispersed on the fiber surface has a boundary.

4. The hemostatic compound of claim 1, wherein the average size of the molecular sieve nanoparticles of the outer surface is larger than the average size of the molecular sieve nanoparticles of the inner surface.

5. The hemostatic compound of claim 1, wherein the average size of the molecular sieve nanoparticles of the inner surface is 2 to 100 nm.

6. The hemostatic compound of claim 1, wherein the average size of the molecular sieve nanoparticles of the outer surface is 50 to 500 nm.

7. The hemostatic compound of claim 2, wherein the non-planar surface is composed of any one or combination of non-planar curves or non-planar lines.

8. The hemostatic compound of claim 1, wherein the molecular sieve is a molecular sieve after metal ion exchange.

9. The hemostatic compound of claim 8, wherein the metal ion is selected from the group consisting of strontium ion, calcium ion, magnesium ion, silver ion, zinc ion, barium ion, potassium ion, ammonium ion, and copper ion, and combination thereof.

10. The hemostatic compound of claim 1, wherein the fiber is a polymer containing hydroxyl groups in a repeating unit.

11. The hemostatic compound of claim 1, wherein the molecular sieves are independently dispersed on the fiber surface means that the minimum distance between the molecular sieve microparticles and the nearest molecular sieve microparticles is greater than or equal to one half of the sum of the particle sizes of the two molecular sieve microparticles, that is:

$$d \geq r1 + r2;$$

where r1 and r2 respectively represent one half of the particle size of two adjacent molecular sieve microparticles; and d represents the minimum distance between two adjacent molecular sieve microparticles.

12. A preparation method for the hemostatic compound of claim 1, wherein the preparation method is an in-situ growth method, and the in-situ growth method comprises the following steps:
(i) preparing a molecular sieve precursor solution and mix the molecular sieve precursor solution with a fiber; the fiber has not been subjected to pretreatment, and the pretreatment refers to a treatment method that destroys fiber structure of the fiber;
(ii) processing the mixture of the fiber and the molecular sieve precursor solution obtained in step (i) with heat treatment to obtain a hemostatic compound.

13. The preparation method of claim 12, wherein the molecular sieve precursor solution does not include a templating agent.

14. The preparation method of claim 12, wherein in the step (ii), the temperature of the heat treatment is 60 to 220° C., and the time of heat treatment is 4 to 240 h.

15. The preparation method of claim 12, wherein in step (i), the mass ratio of the fiber to the molecular sieve precursor solution is 1:0.5 to 1:1000.

16. A composite material, wherein the composite material comprises the hemostatic compound according to claim 1.

17. The composite material of claim 16, wherein the composite material is a hemostatic textile.

18. The composite material of claim 17, wherein the hemostatic textile is selected from the group consisting of a hemostatic bandage, a hemostatic gauze, a hemostatic cloth, a hemostatic clothing, a hemostatic cotton, a hemostatic suture, a hemostatic paper, a hemostatic band-aid, and combination thereof.

* * * * *